( 12 ) United States Patent
Jeppesen et al.

(10) Patent No.: US 8,378,093 B2
(45) Date of Patent: Feb. 19, 2013

(54) EXPLOSIVES DETECTION MARKERS

(75) Inventors: Jan Oskar Jeppesen, Odense (DK); Kent A. Nielsen, Odense (DK)

(73) Assignee: Syddansk Universitet, Osense (DK)

( * ) Notice: Subject to any disclaimer, the term of this patent is extended or adjusted under 35 U.S.C. 154(b) by 1269 days.

(21) Appl. No.: 11/748,534

(22) Filed: May 15, 2007

(65) Prior Publication Data

US 2011/0003396 A1   Jan. 6, 2011

(30) Foreign Application Priority Data

May 15, 2006 (DK) .................................. 2006 00678

(51) Int. Cl.
*C07D 487/22* (2006.01)
*C07D 339/06* (2006.01)
*G01N 30/96* (2006.01)
(52) U.S. Cl. ............................. 540/145; 422/69; 549/31
(58) Field of Classification Search .................. 540/145; 422/69; 549/31
See application file for complete search history.

(56) References Cited

FOREIGN PATENT DOCUMENTS

WO           01/77664 A1    10/2001
WO    WO 01/77664 A2 *   10/2001

OTHER PUBLICATIONS

Nielsen et al. "Tetra-TTF Calix[4]pyrrole: A Rationally Designed Receptor for Electron-Deficient Neutral Guests" Journal of the American Chemical Society, 2004, vol. 126, pp. 16296-16927.*
Kent A.Nielsen et. al., "Tetra-TTF Calix[4] pyrrole: A rationally designed receptor for electron deficient neutral guests," Journal of the American Chemical Society 2004 126:16296-16297, American Chemical Society, USA.

* cited by examiner

*Primary Examiner* — Joseph Kosack
(74) *Attorney, Agent, or Firm* — Birch, Stewart, Kolasch & Birch, LLP

(57) ABSTRACT

The present invention relates to a porphyrinogen based sensor having selective binding affinity for an explosive chemical. Upon binding of the target molecule, the porphyrinogen derivative undergoes a detectable adsorption and emission of electromagnetic radiation.

13 Claims, 25 Drawing Sheets

Fig. 7

Scheme 1

1,3-Alternate Conformation        Cone Conformation

Scheme 2

Scheme 3

Scheme 4

Scheme 5

Scheme 6

Scheme 7

Scheme 8

Scheme 9

Scheme 10

Scheme 11

Scheme 12

Scheme 13

Scheme 14

Scheme 15

Scheme 16

Scheme 17

Scheme 18

EXPLOSIVES DETECTION MARKERS

BACKGROUND OF THE INVENTION

The present invention relates to a porphyrinogen based sensor having selective binding affinity for an explosive chemical. More particularly, this invention is directed to a porphyrinogen derivative possessing cavities which selectively bind the target molecule when the sensor is exposed to environments containing the target molecule. Upon binding of the target molecule, the porphyrinogen derivative undergoes a detectable adsorption and emission of electromagnetic radiation. Moreover, the invention relates to the formation on a metal surface of a self assembled molecular monolayer (SAM) that exposes the porphyrinogen derivative of the present invention to an analyte medium in a manner such that analysis of high sensitivity is obtained.

Chemical sensors must normally fulfill two goals: (1) the development of a specific chemical recognition element that allows a molecule, or class of molecules, to be identified, and (2) a means of signal transduction in which the presence of the molecule causes a measurable change in a physical property of the material. Although these goals are not always separable, the successful design of chemical sensors requires that both is being satisfied. Most transduction approaches are based on optical, resistive, surface acoustic wave, or capacitive measurements. These well-developed methods dominate largely because of their ease of operation, sensitivity, and cost. The chemical recognition elements in these detectors, however, lag far behind.

In a typical sensor fabrication, a solid plastic mass, consisting of the matrix and binder, is prepared which is chemically bound to the polymer/cross-linker matrix and the target molecule. Removal of the target is possible since it is reversibly bound to the binder. The cavity it leaves behind is permanently shaped like the target. Methods for the detection of explosives and explosive residues require complex analytical instruments such as liquid or gas chromatographs coupled with mass spectroscopic or chemiluminescent detection. The associated instrumentation is usually large, expensive, difficult to maintain and requires skilled operators. If laboratory analysis is necessary, extensive documentation is needed for sample transport, increasing the possibility of sample contamination. Immunoassay tests are available for some explosives, but these are cumbersome and have short shelf lives.

A large number of organic pollutants are found in soil. Examples are xenobiotic compounds containing nitro functional groups, which are used in the production of agricultural chemicals, pharmaceuticals, dyes and plastics. Such compounds are also used in mining, farming and they are the main charge in ammunition including landmines. The most common residues contain 2,4,6-trinitrotoluene (TNT), hexahydro-1,3,5-trinitro-1,3,5-triazine (RDX), octahydro-1,3,5,7-tetranitro-1,3,5,7-tetrazocine (HMX), and associated impurities and environmental transformation products.

Such compounds contaminate their sites of manufacture and storage as well as military installations. In addition, it is estimated that approximately 90% of the mines currently in use are leaking, resulting in the spread of TNT into the soil. Unlike many other pollutants, some of these contaminants have little affinity for soils and rapidly migrate to pollute groundwater. This is a concern as high levels of TNT have been observed to have the potential to inhibit biological activity. Besides the direct consequences of the pollution itself, pollutants of this type may be an indication of the presence of explosives. As landmines are killing and maiming people in former war zones, particularly in remote and poor parts of the world, knowledge of their presence would be of great humanitarian value.

A first requirement in dealing with soil pollution, is an ability to detect polluted sites. Detection systems that are practical and relatively inexpensive are desirable, in order to facilitate their wide-spread use. The currently available detection methods allow for the detection of pollutants, but the methods are both inconvenient and costly.

When referring to information concerning a soil sample each observation relates to a particular location and time. Knowledge of an attribute value, say a pollutant concentration, is thus of little interest unless location and/or time of measurement are known and accounted for in the analysis. The key decisions to achieve cost-effective, accurate site characterizations are the number, location and type of soil samples to be collected, Site characterization errors occur when the sample does not accurately represent the area which the modeling plan assumes it represents. This is a particular problem when the contaminant is distributed non-homogeneously throughout the soil, as occurs with e.g. explosives contamination.

Thus, the characterization of contaminated soils can be expensive and time consuming due to the large number of samples required to effectively evaluate a site.

Present laboratory methods of evaluating environmental samples offer high sensitivity and the ability to evaluate multiple chemicals, but the time and cost associated with such methods often limit their effectiveness. Thus, for many applications there exists a requirement for an economically feasible, robust, and rapid responding system for the mapping of contaminated soils.

Soil contaminated by explosives are traditionally monitored by collecting samples which are analysed in a laboratory by applying various techniques, such as Enzyme Immunoassay and High Performance Liquid Chromatography.

The detection of landmines is normally carried out by sweeping the concerned area using metal-detectors, dogs or manual labour. In military demining, the objective is to clear a minefield as fast as possible using brute force, and usually a clearance rate of 80-90% is accepted. Humanitarian demining, on the other hand, is more difficult and dangerous, as it requires the complete removal of all mines and the return of the cleared minefield to normal use, Today, most humanitarian demining is done using handheld metal detectors finding objects containing metal by utilizing a time varying electromagnetic field to induce eddy-currents in the object, which in turn generates a detectable magnetic field. Old landmines contain metal parts (e.g., the firing pin), but modern landmines contain very small amounts or no metal at all. Increasing the sensitivity of the detector to detect smaller amounts of metal also makes it very sensitive to metal scrap often found in areas where mines may be located. Furthermore, metal detectors, however sophisticated, can only succeed in finding anomalies in the ground without providing information about whether an explosive agent is present or not, One major problem in humanitarian demining is to discriminate between a "dummy" object and a landmine, Identifying and removing a harmless object is a time-consuming and costly process. Dogs have extremely well-developed olifactory senses and can be trained to detect explosives in trace quantities. This technique, however requires extensive training of the dogs and their handlers, and the dog's limited attention span makes it difficult to maintain continuous operations. A number of mine detection techniques are emerging as complements to presently used methods. They include ground penetrating radar (GPR), infrared thermography and advanced metal detectors. A common feature of these techniques is that they detect "anomalies" in the ground but are unable to indicate the presence of an explosive agent. Basically, GPR systems work by emitting a short electromagnetic pulse in the ground through a wideband antenna. Reflections from the ground are then measured to form a vector. The displacement of the antenna allows to build an image by displaying successive vectors side by side. High frequencies are needed to achieve a good spatial resolution, but penetration depth of electric fields being inversely proportional to the frequency, too high frequencies are useless after some centimeters.

Hence, the choice of the frequency range is a trade-off between resolution and penetration depth. Although the detectors can be tuned to be sensitive enough to detect the small amount of metal in modern mines, this is not practically feasible, as it will also lead to the detection of smaller debris and augment the false alarms rate.

WO0177664A2 discloses a so-called molecularly imprinted polymeric explosives sensor. The sensor possesses selective binding affinity for explosives, such as 2,4,6-trinitrotoluene (TNT) and 1,3,5-trinitrobenzene (TNB). The polymeric sensor incorporates a porphyrin unit which undergoes a detectable change in absorption and/or emission of electromagnetic radiation when the polymer is exposed to explosives. However, the document does not disclose the tetra-TTF calix[4]pyrrole used in the present invention.

WO03031953A2 discloses a method and apparatus for sensing nitroaromatics. The subject method can utilize luminescent, for example fluorescent and/or electroluminescent, aryl substituted polyacetylenes and/or other substituted polyacetylenes which are luminescent for sensing nitroaromatics. In a specific embodiment, the subject method utilizes thin films of fluorescent and/or electroluminescent aryl substituted polyactylenes and/or other substituted polyacetylenes which are fluorescent and/or electroluminescent. The document does not disclose the tetra-TTF calix[4]pyrrole used in the present invention.

WO0177650A1 discloses a method for detecting an analyte in a sample, using surface enhanced (resonance) Raman scattering (SE(R)RS) detection, comprising the steps of a) mixing the sample with a reagent such that any analyte present in the sample reacts with the reagent thereby forming a derivatised analyte, wherein the derivatised analyte comprises a chromophore; b) mixing said derivatised analyte with a SE(R)RS active substrate so as to adhere the derivatised analyte thereto; and C) detecting the derivatised analyte by way of SE(R)RS detection whereby any derivatised analyte detected may be correlated with analyte present in the sample. Examples of analytes which may be detected include, aldehydes, amines, explosives, drugs of abuse, therapeutic agents, metabolites and environmental pollutants. The sample may be any suitable preparation in which the target analyte is likely to be found. However, the sample may conveniently be in solution or transferred to a solution before reacting with the reagent. Thus, for example when detecting explosives or drugs of abuse, a sample of air or breath respectively, may be taken and any target analyte absorbed onto a suitable substrate. Thereafter, any target analyte may be removed from the substrate by washing with a suitable solvent, such as dimethylformamide (DMF), acetone or tetrahydrofuran (THF). For example, in the determination of TNT or RDX from the vapour phase, the vapour can first be collected on a suitable material such as tenax and a small amount of solvent washed through the material to produce a small amount of explosive in solution. The preferred solvent for this purpose is dimethylformamide.

WO0026638A1 discloses a sensor for detecting an analyte in a fluid comprising a substrate having a first organic material and a second organic material that has a response to an analyte. The sensor has information storage and processing equipment, and a fluid delivery appliance. This device compares a response from the detector with a stored ideal response to detect the presence of analyte. Methods for use for the above system are described where the first organic material and the second organic material are sensed and the analyte is detected. The method provides for a device, which delivers fluid to the sensor and measures the response of the sensor with the detector. Further, the response is compared to a stored ideal response for the analyte to determine the presence of the analyte. In different embodiments, the fluid measured may be a gas, a liquid, or a fluid extracted from a solid. Eventhough the document mentions the applicability of sensor substrates comprising polymers, such as poly(anilines), poly(thiophenes), and poly(pyrroles), there is no suggestion that the specific tetra-TTF calix[4]pyrrole envisaged by the present invention will be applicable for the sensing of TNT.

US20040234958A1 discloses a method for detecting an analyte in a sample using surface enhanced (resonance) Raman scattering (SE(R)RS) detection, comprising the steps of a) mixing the sample with a reagent such that any analyte present in the sample reacts with the reagent thereby forming a derivatised analyte, wherein the derivatised analyte comprises a chromophore; b) mixing said derivatised analyte with a SE(R)RS active substrate so as to adhere the derivatised analyte thereto; and c) detecting the derivatised analyte by way of SE(R)RS detection whereby any derivatised analyte detected may be correlated with analyte present in the sample.

Considerable effort has been focused on the preparation of supramolecular host systems with the capability of recognizing specific chemical species through weak, noncovalent interactions. The incorporation of redox-active components into host molecules is one means of enhancing the guest recognition process via, for instance, increased donor-acceptor interactions. In this context, the use of tetrathiafulvalene (TTF) appears particularly attractive. To date, a number of TTF-containing systems have been synthesized to study host-guest binding events. However, in almost all cases, only weak interactions were observed with neutral guests.

The present inventors have published a paper (J. AM. CHEM, SOC. 2004, 126, 16296-16297) disclosing one of the porphyrinogen derivatives of the present invention, namely the compound of claim 1, which has been excluded from protection (tetra-TTF calix[4]-pyrrole 2a). However, the prior art known to the inventors does not disclose the use of tetra-TTF calix[4]-pyrrole for the detection of explosives, e.g. by interaction with TNT.

The present inventors have surprisingly found that tetra-TTF calix[4]-pyrrole as well as the porphyrinogen derivatives of the present invention have superior properties with respect to the sensing of explosive chemicals, such as TNT.

SUMMARY OF THE INVENTION

The present invention provides a porphyrinogen derivative (e.g. tetra-TTF calix[4]pyrrole) which selectively binds a target molecule which comprises an explosive chemical. More specifically the present invention is directed against porphyrinogen derivative of the general formula 2

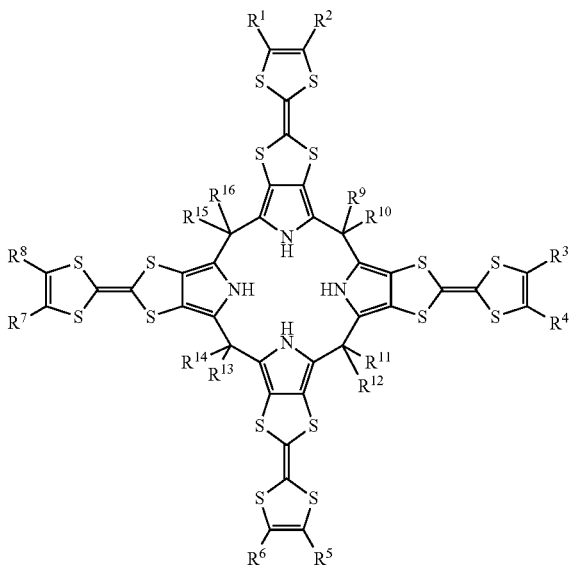

wherein $R^1$-$R^{16}$ independently represents any organic or inorganic group with the proviso that protection is excluded for the compound, wherein $R^1$-$R^8$ is exclusively —S—CH2-CH3 and $R^9$-$R^{18}$ is exclusively methyl.

This would thus include porphyrinogen derivatives of the general formula 2 wherein $R^1$-$R^8$ is independently selected from the group consisting of
  i) $SR^A$ in which $R^A$ represents an alkyl chain from C1 to C20 or a —CH$_2$CH$_2$—O—(CH$_2$CH$_2$O)$_n$ group in which n=0-5;
  ii) $COOR^B$ in which $R^B$ represents an alkyl chain from C1 to C20 or a —CH$_2$CH$_2$—O—(CH$_2$CH$_2$O)$_n$ group in which n=0-5;
  iii) CH$_2$Ar, in which Ar represents an aryl group; and
  iv) CH$_2$XR$^C$ in which X represents and O, S, or N atom and $R^3$ represents an alkyl chain from C1 to C20 or a —CH$_2$CH$_2$—O—(CH$_2$CH$_2$O)$_n$ group in which n=

The present invention is based on the capability of the porphyrinogen derivative of the present invention to selectively bind explosive markers. This derivative acts as an effective receptor for neutral electron acceptors, such as 1,3,5-trinitrobenzene (TNB), 1,3-dinitrobenzene (1,3-DNB), 2,4,6-trinitrotoluene (TNT), 2,4-dinitrotoluene (2,4-DNT), 2,6-dinitrotoluene (2,6-DNT), 2,4,6-trinitrophenole (TNP), 2,4-dinitrophenole (2,4-DNP), 2,6-dinitrophenole (2,6-DNP), tetrafluoro p-benzoquinone, tetrachloro-p-benzoquinone, and p-benzoquinone, in solution and in the case of TNB, TNT, and tetrafluoro p-benzoquinone also in the solid state. This neutral substrate recognition process can be blocked by the addition of chloride anion.

Prior to this work, few reports of neutral substrate binding by calix[4]pyrroles had appeared. The porphyrinogen derivative of the present invention has been designed to take advantage of the fact that calix[4]pyrroles generally exist in the 1,3-alternate conformation in the absence of anions. In this conformation, each pair of identical TTF electron donors is expected to hold an electron deficient guest in a sandwichlike fashion via charge transfer (CT) interactions, Additional stabilization is also expected to be provided by the pyrrole NH hydrogen bond donors and π-π stacking.

Also provided in accordance with the invention is a spectroscopic sensor comprising the porphyrinogen derivative of the invention. The sensor may comprise a fiber optic or other waveguide sensor for detecting the presence of target molecules comprising explosives, such as TNT, TNB, and TNP, as well as analogs and degradents thereof, the sensor comprising: at least one optical fiber means having a proximal end and a distal end for transmitting light energy, the proximal end being disposed within a probe housing, the porphyrinogen derivative of the invention disposed on or bonded to the distal end of the optical fiber means, wherein the porphyrinogen derivative is capable of chemically binding with the target molecule, light source means for generating excitation energy, said light source means being operatively associated with said optical fiber means such that said excitation light passes through said optical fiber means, and detection means operatively associated with the optical fiber means, for detecting an emission and/or absorption signal generated by said polymer.

In another embodiment, the present invention is directed to a surface acoustic wave sensor for detecting the presence of an explosive, the sensor having been adapted to comprise the porphyrinogen derivative bound thereto. In particular, the surface acoustic wave sensor of the present invention comprises a film of the porphyrinogen derivative of the present invention disposed on a substrate such as alumina or a piezocrystal substance, such as quartz crystal, wherein the porphyrinogen derivative is capable of chemically binding with fluids containing an explosive; input and output transducers disposed on the film or substrate; and a function generator operatively associated with the input transducer for generating a surface acoustic wave along a delay line.

Additional aspects, embodiments and advantages of the present invention will be set forth, in part, in the description that follows, or may be learned from practising or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

The term "fluid" is used herein in the broadest sense, i.e., as referring to include gases such as vapors and liquids such as, for example, water, solvents, and the like.

BRIEF DESCRIPTION OF FIGURES

FIG. 7. Test showing the color change before (left picture) and after (middle and right pictures) spraying an aerosol of the tetra-TTF calix[4]pyrrole 2a dissolved in $CHCl_3$ unto sand containing a small quantity of TNB. Examples 1 and 2 represent two independent experiments.

FIG. 10. Synthesis of the tetra-TTF calix[4]pyrrole derivative 2a.

DESCRIPTION OF THE PREFERRED EMBODIMENTS

Figure 1:
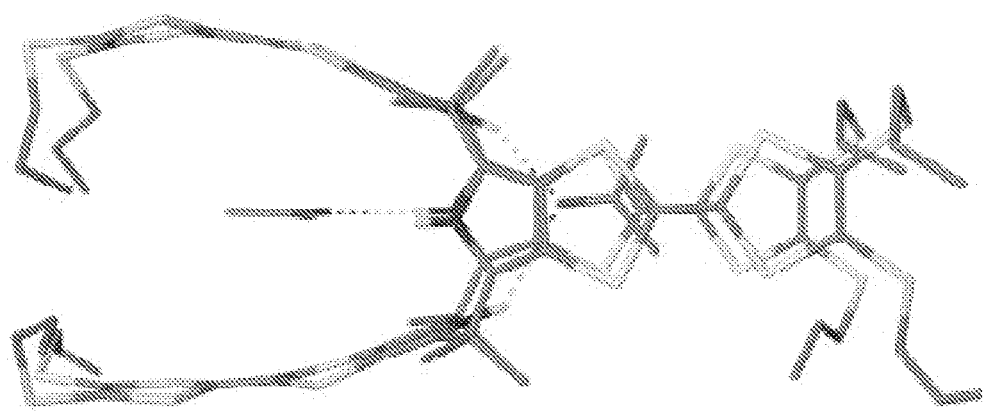
FIG. 1. X-Ray crystal structure of a porphyrinogen derivative, 2a, of the present invention.

As used herein, the term porphyrinogen derivative of the present invention refer to a molecular mold-like structure that has preorganized interactive moieties complementing the spacing of binding sites on a target molecule comprising an explosive chemical such as 2,4,6-trinitrotoluene (TNT), 1,3, 5-trinitrobenzene (TNB), and 1,3,5-trinitrophenole (TNP). The interactive moieties possess a geometrical organization which imparts selective binding characteristics for the explosive chemical. The term "selective binding" is intended to refer to preferential and reversible binding exhibited by the porphyrinogen derivative herein for the explosives chemical compared to non-template molecules having similar structures, e.g., insecticides such as chloro-nitro-benzenes. Selective binding includes both affinity and specificity of the porphyrinogen derivative of the present invention for the explosives chemical.

The invention also provides a method for detecting an explosive, comprising: exposing the porphyrinogen derivative of this invention to an environment containing explosives such that vapors and/or particulate emissions from the explosive come in contact with the porphyrinogen derivative, and detecting any change in absorption and/or emission of electromagnetic radiation by the porphyrinogen derivative, said detected change being indicative of the presence of explosive in, on, or in association with said environment.

In a preferred embodiment, the porphyrinogen derivative of the present invention may be bound to a suitable, substrate, such as, for example, a dosimeter-like badge worn by a person, animal or machine, for the detection of explosive vapors. When the person or animal wearing the badge enters an area containing vapors of an explosive, the vapors of the explosive bind to the porphyrinogen derivative thereby causing it to absorb and/or emit radiation.

In yet another preferred embodiment, the present invention is directed to a fiber optic sensor device for detecting the presence of a target molecule comprising an explosive such as TNT, TNB, or TNP as well as analogs and degradents thereof, the sensor comprising at least one optical fiber means having a proximal end and a distal end for transmitting light energy, the proximal end being disposed within a probe housing, the porphyrinogen derivative of this invention disposed on, or bonded to, the distal end of the optical fiber means, wherein the derivative is capable of chemically binding with said target molecule, light source means for generating excitation energy, said light source means being operatively associated with said optical fiber means such that said excitation light passes through said optical fiber means, and detection means operatively associated with said optical fiber means, for detecting an absorption and/or emission signal generated by said polymer.

Suitable non-limiting examples of light source means include an argon laser, blue laser, tunable laser, light emitting diode (LED), and the like.

Suitable non-limiting examples of detection means include a spectrophotometer, spectrometer (gas or mass), photomultiplier tube, monochromator equipped with a CCD camera, quartz crystal microbalance (QCM), filters, the naked eye, and the like.

In this embodiment, the portable device may employ a modulated laser diode for excitation and a small photosensor module for detection, with the output going to a microprocessor controlled grated integrator. In addition, an optical multiplex switch may be incorporated into the design so that many sensors can be coupled to one control system, which will allow monitoring of a large area such as found in a building, subway station, shopping mall, airport, etc.

In use, vapors or particulate emissions of an explosive or a liquid containing an explosive, if present, bind to the porphyrinogen derivative of the present invention causing it to change colour. Light from the light source means travels along the optical fiber to its distal end where it undergoes a change caused by interaction with the porphyrinogen derivative. The modified light returns along the same or another fiber to the detection means which interprets the returned light signal. Detection is based on the change that occurs in the polymer's absorption spectrum when vapor of an explosive binds to the polymer.

Optionally, the distal end (working end) of the sensor may be enclosed within a semi-permeable membrane to separate the explosive-containing media being analyzed from the probe. One function of the membrane is to separate, as far as possible, the explosive (i.e., those components in a sample that can bind to the probe) from interferents (i.e., compounds which may be present but are undesirable because they either interfere with the progress of the desired determination reactions or take part in reactions of their own which compete with those of the explosive whose detection is being sought and distort or overwhelm the signals that are to be measured).

In yet another preferred embodiment, the present invention is directed to a SAW (Surface Acoustic Wave) sensor for detecting the presence of vapors or particulate emissions of an explosive or liquids containing an explosive. The SAW sensor comprises the porphyrinogen derivative of the present invention bound thereto.

Another purpose of the present invention is to provide an easily-synthesized chemical species that readily adheres to a surface, and that facilitates surface immobilization of a binding partner of a molecule desirably captured at the surface with a high degree of sensitivity and minimal to zero non-specific binding. In this respect Self assembled monolayers (SAMs) provide a convenient way to achieve such immobilization. As will be recognized by one skilled in the art porphyrinogen derivative of the present invention may be immobilized or bonded to e.g. a gold surface if the porphyrinogen has at least one accessible (i.e. not sterically hindered) —SH group (thiol). Accordingly, the present invention is also directed to porphyrinogen derivative of the general formula 2 (see above and claim 1), wherein at least one of the side groups (R) has a free thiol group available for binding to the surface.

The term "self assembled monolayer" refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis, P. E.; Hickman, J.; Wrighton, M. S.; Whitesides, G. M. Science 245, 845 (1989), Bain, C.; Evall, J.; Whitesides, G, M. *J. Am. Chem. Soc,* 111, 7155-7164 (1989), Bain, C.; Whitesides, G. M. *J. Am. Chem. Soc.* 111, 7164-7175 (1989), and J. Christopher Love, Lara A. Estroff, Jennah K Kriebel, Ralph G. Nuzzo, and George M. Whitesides *Chem. Rev.* 105, 1103-1169 (2005) each of which is incorporated herein by reference.

In certain aspects of the present invention, multiple of the above mentioned sensor types are integrated into a high density platform, preferably on a silicon chip, or other substrate material as is well known. In preferred aspects, the sensors are integrated onto a single chip.

EXAMPLES

Example 1

Synthesis and Characterization of the Tetra-TTF Calix[4]Pyrrole 2a

Figure 4:
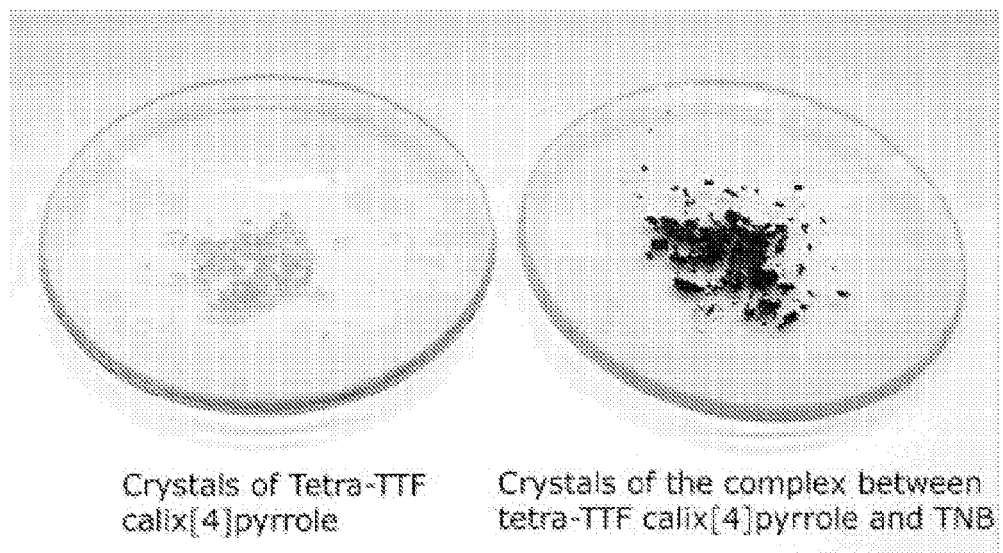
FIG. 4. Picture showing the color change from yellow to black in the solid state that takes place upon complexation between the tetra-TTF calix[4]pyrrole 2a and TNB.

A general approach to the synthesis of the tetra-TTF calix[4]pyrrole (porphyrinogen derivative of the present invention) is outlined in Scheme 1, Treating the monopyrrolo-TTF 1a with an excess of TFA in a mixture of $CH_2Cl_2$ and $Me_2CO$ gave the tetra-TTF calix[4]pyrrole 2a as a yellow solid in 18% yield. It was fully characterized including an X-ray crystal structure analysis (FIG. 1). Crystals suitable for X-ray crystallography were made by slow diffusion of a $Me_2CO$ layer into a $CH_2Cl_2$ solution containing tetra-TTF calix[4]pyrrole, affording 2a as yellow needles (FIG. 4).

Figure 2:
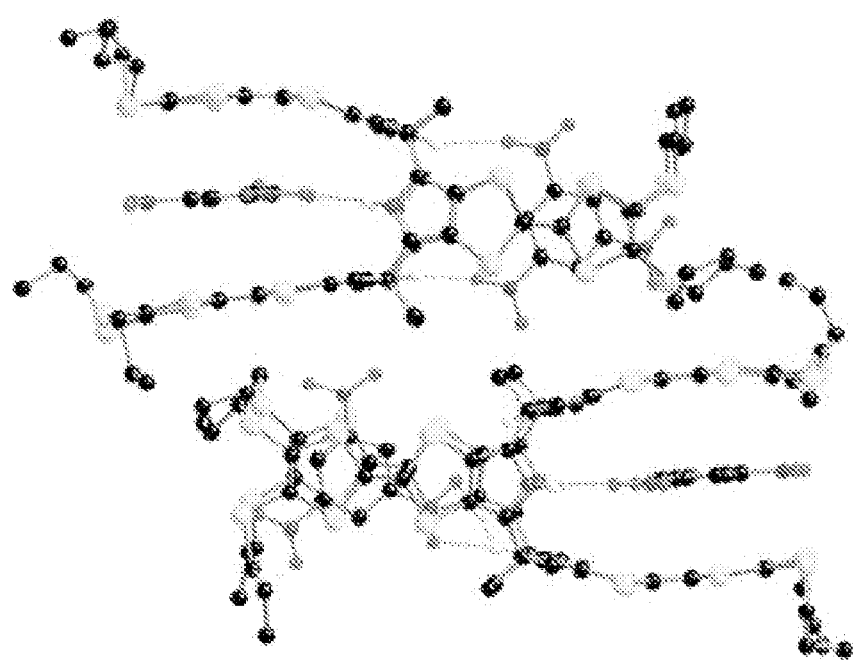
FIG. 2. X-Ray crystal structure illustrating the H-bonding interactions (dashed lines) between TNB and a porphyrinogen derivative, 2a, of the present invention.
Figure 3:
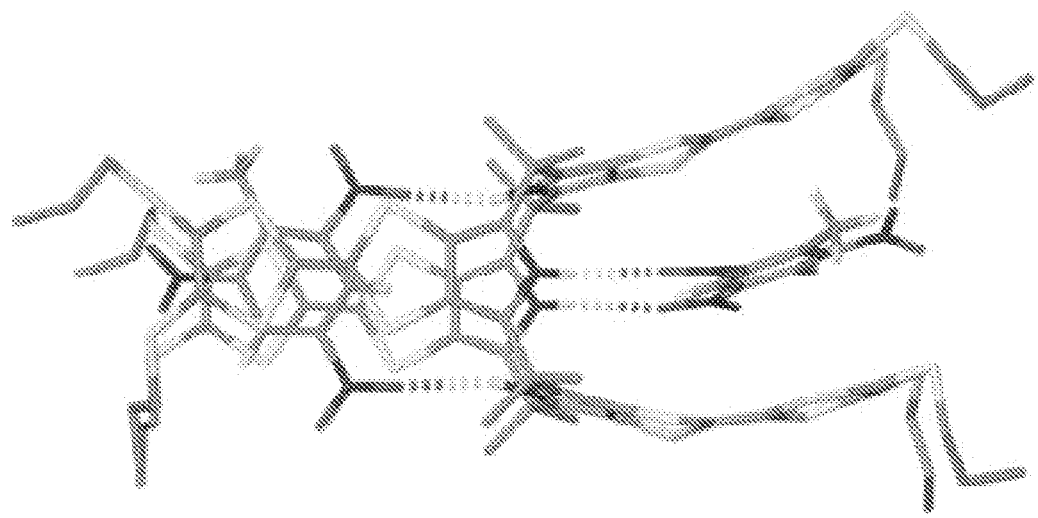
FIG. 3. X-ray crystal structure showing the complexation between the tetra-TTF calix[4]pyrrole 2a and two TNT molecules in the solid-state.
Figure 5:
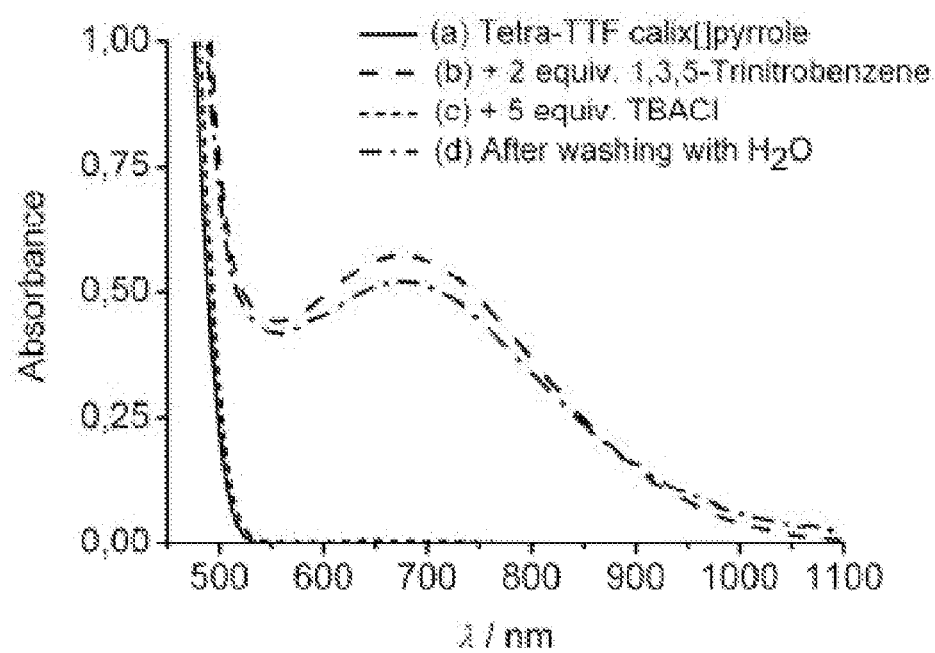
FIG. 5. Absorption spectra (CH$_2$Cl$_2$, 25° C.) of (a) tetra-TTF calix[4]pyrrole 2a (1.0 mM), (b) tetra-TTF calix[4]pyrrole 2a+2 equiv of TNB, (c) tetra-TTF calix[4]pyrrole 2a+2 equiv of TNB+5 equiv of tetrabutylamonium chloride (TBACl), and (d) after washing with H$_2$O.
Figure 6:
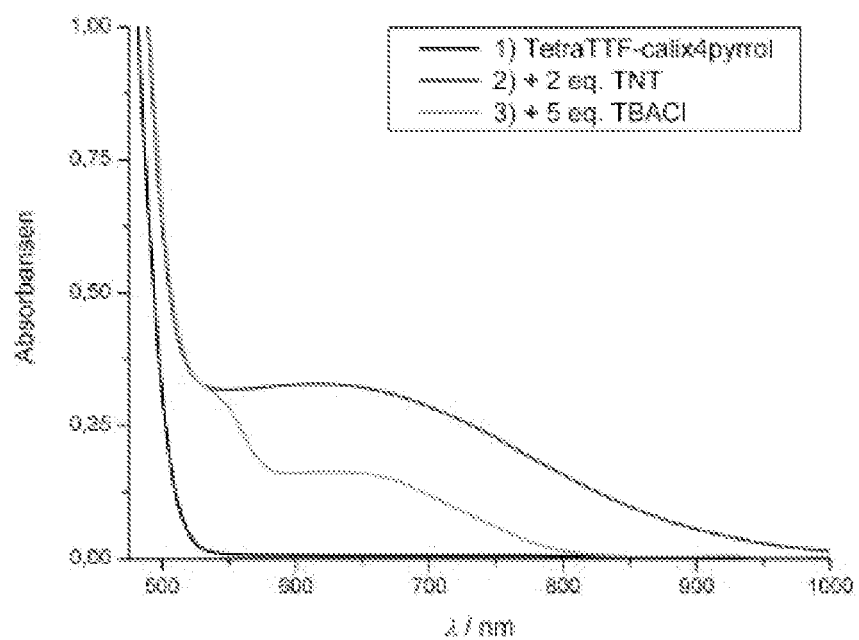
FIG. 6. Absorption spectra (CH$_2$Cl$_2$, 25° C.) of (a) tetra-TTF calix[4]pyrrole 2a+2 equiv of TNT, and (c) tetra-TTF calix[4]pyrrole 2a+2 equiv of TNB+5 equiv of tetrabutylamonium chloride (TBACl).
Figure 8:
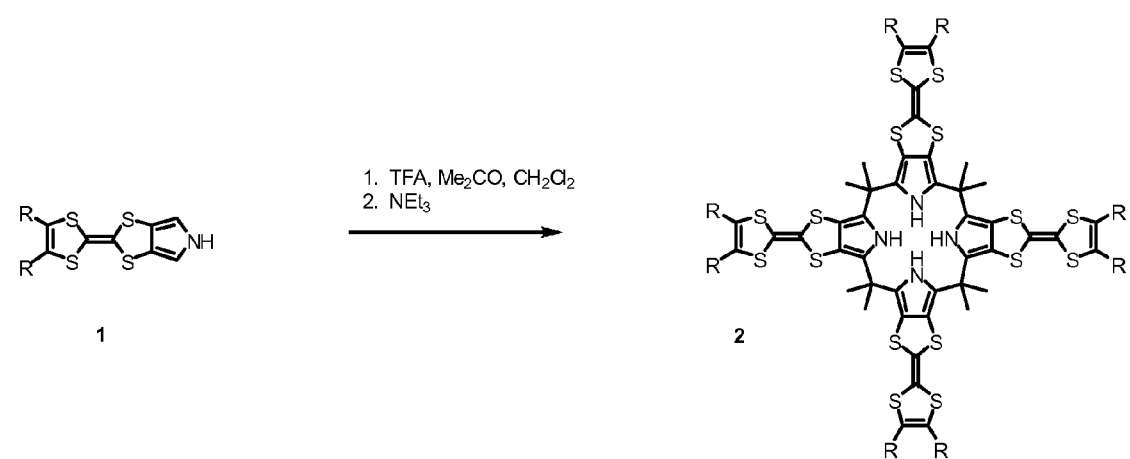
FIG. 8. General approach to the synthesis of the porphyrinogen derivatives (tetra-TTF calix[4]pyrroles) of the present invention.
Figure 9:
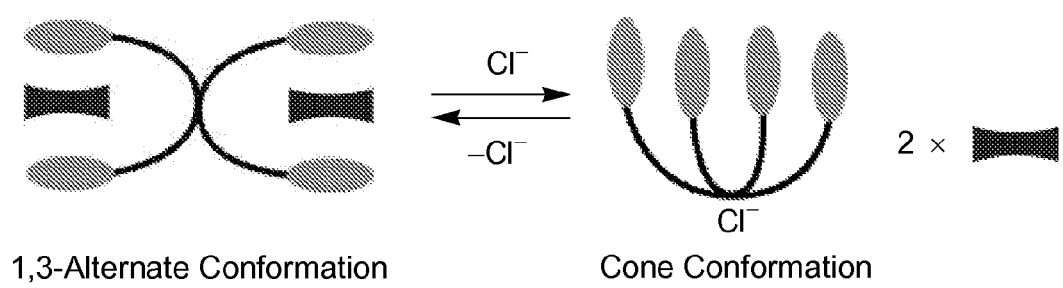
FIG. 9. Cartoon representation illustrating the change in conformation associated with the addition/removal of chloride anion to a $CH_2Cl_2$ solution of the tetra-TTF calix[4]pyrrole and the electron-deficient guest TNB or TNT (represented by the distorted rectangle).
Figure 10:
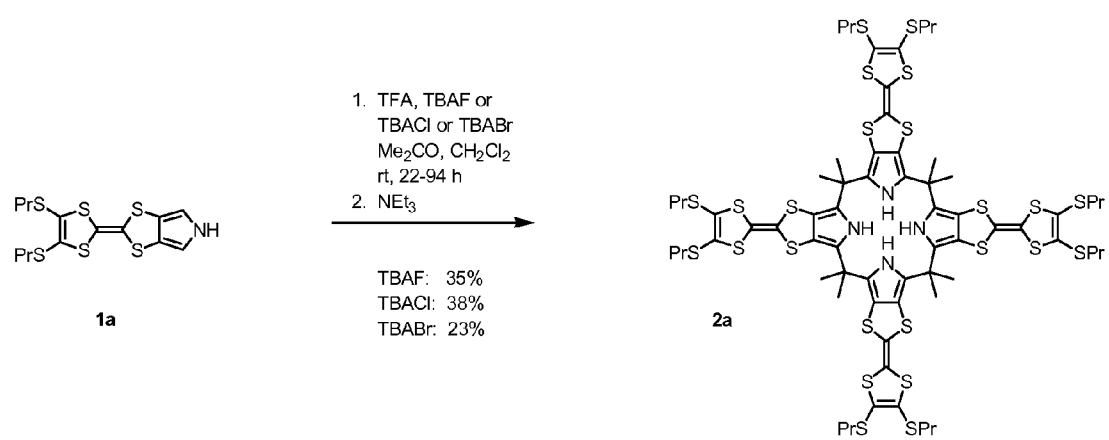
Figure 11:
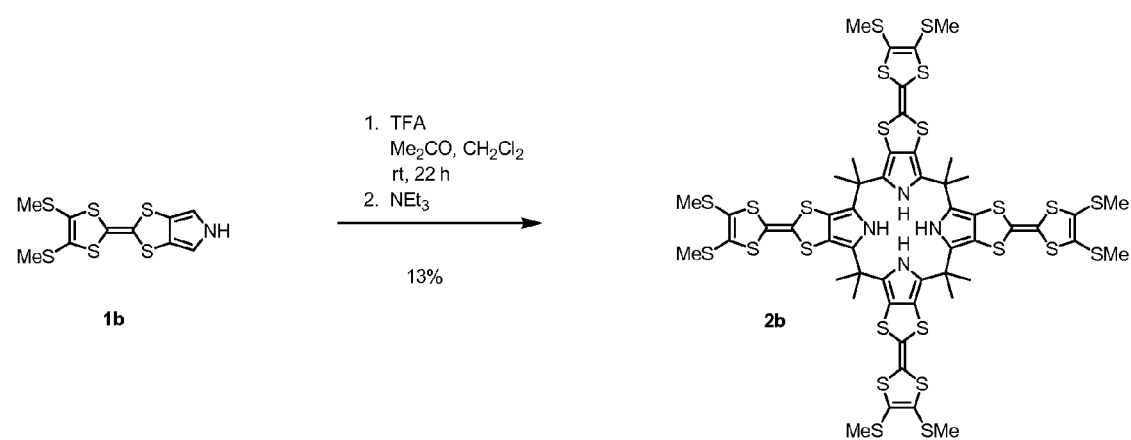
FIG. 11. Synthesis of the tetra-TTF calix[4]pyrrole derivative 2b.
Figure 12:
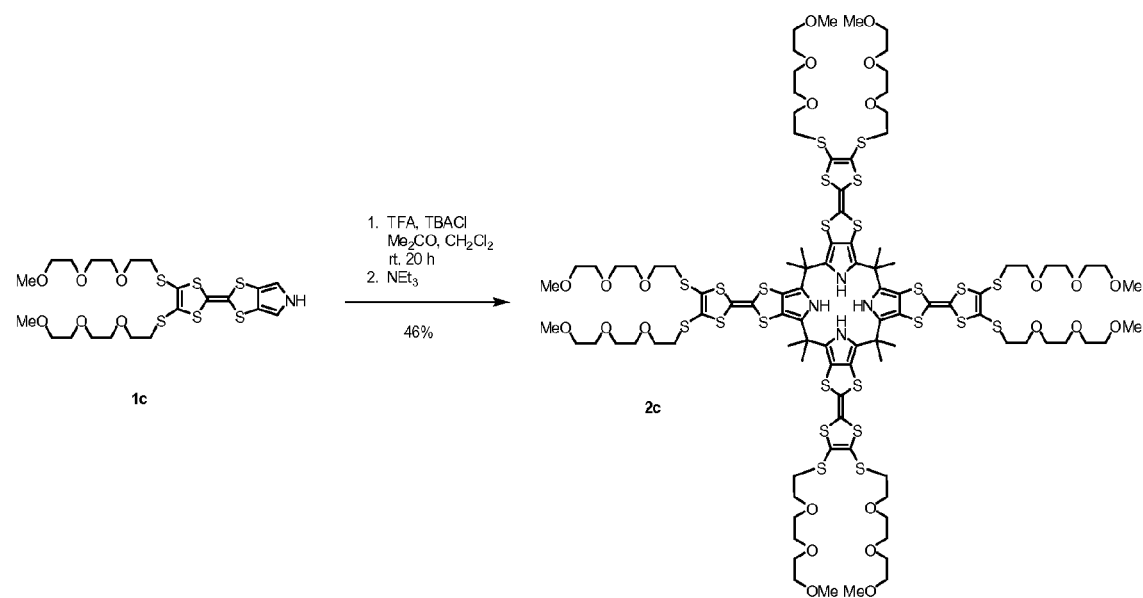
FIG. 12. Synthesis of the tetra-TTF calix[4]pyrrole derivative 2c.
Figure 13:
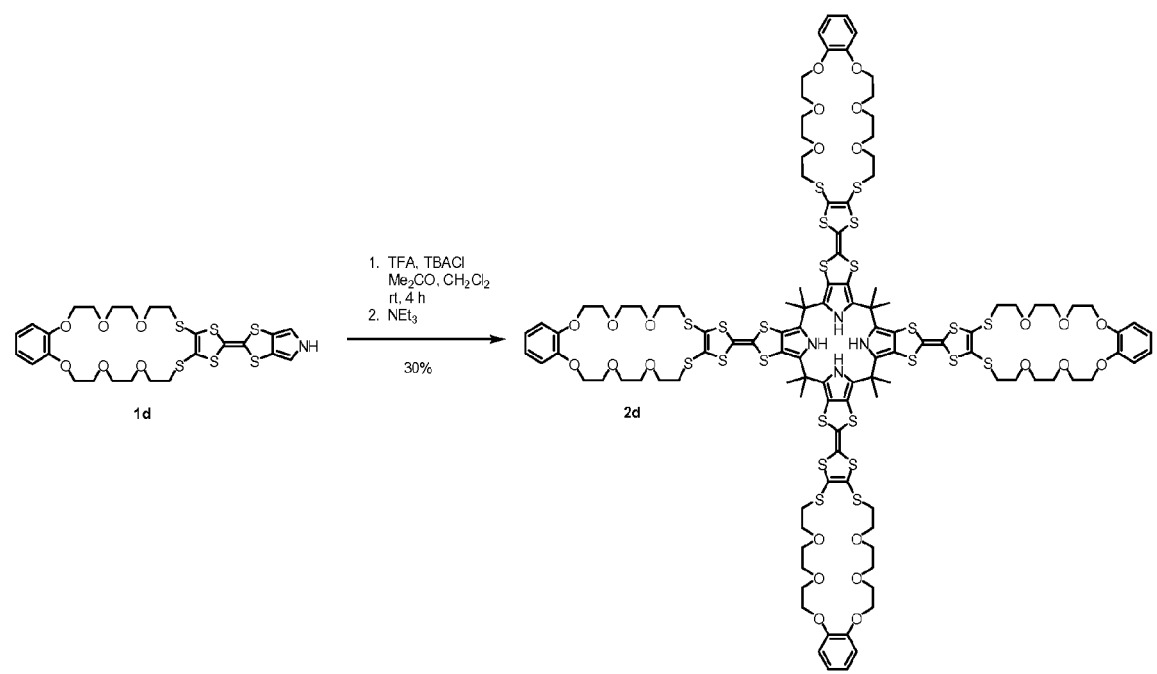
FIG. 13. Synthesis of the tetra-TTF calix[4]pyrrole derivative 2d.
Figure 14:
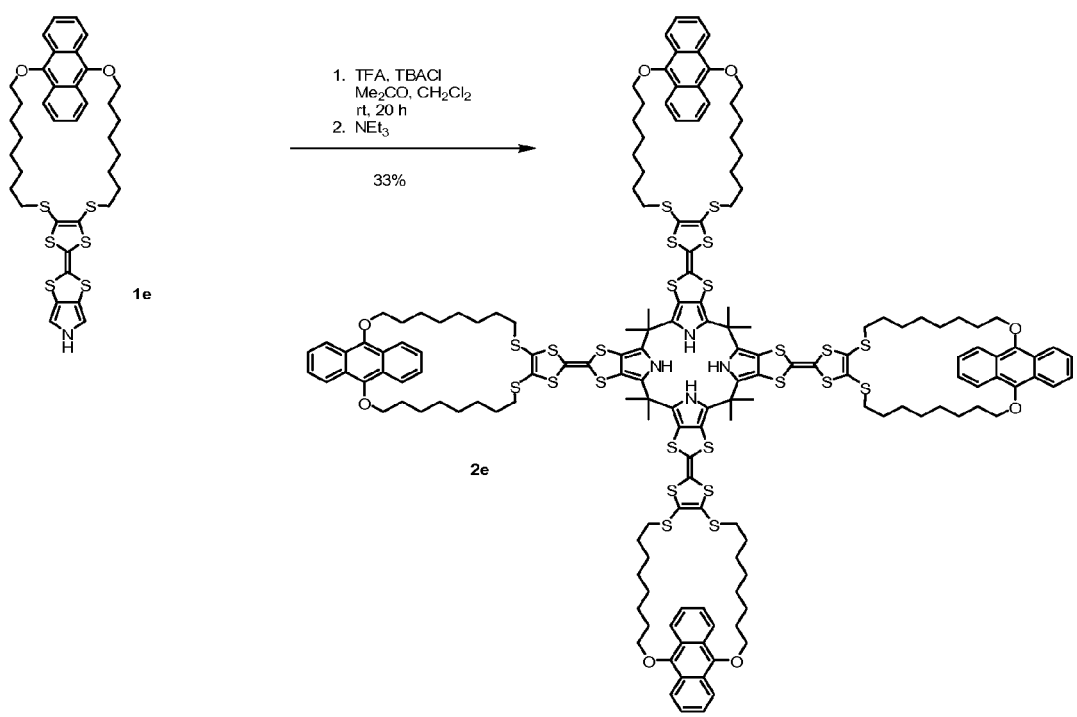
FIG. 14. Synthesis of the tetra-TTF calix[4]pyrrole derivative 2e.
Figure 15:
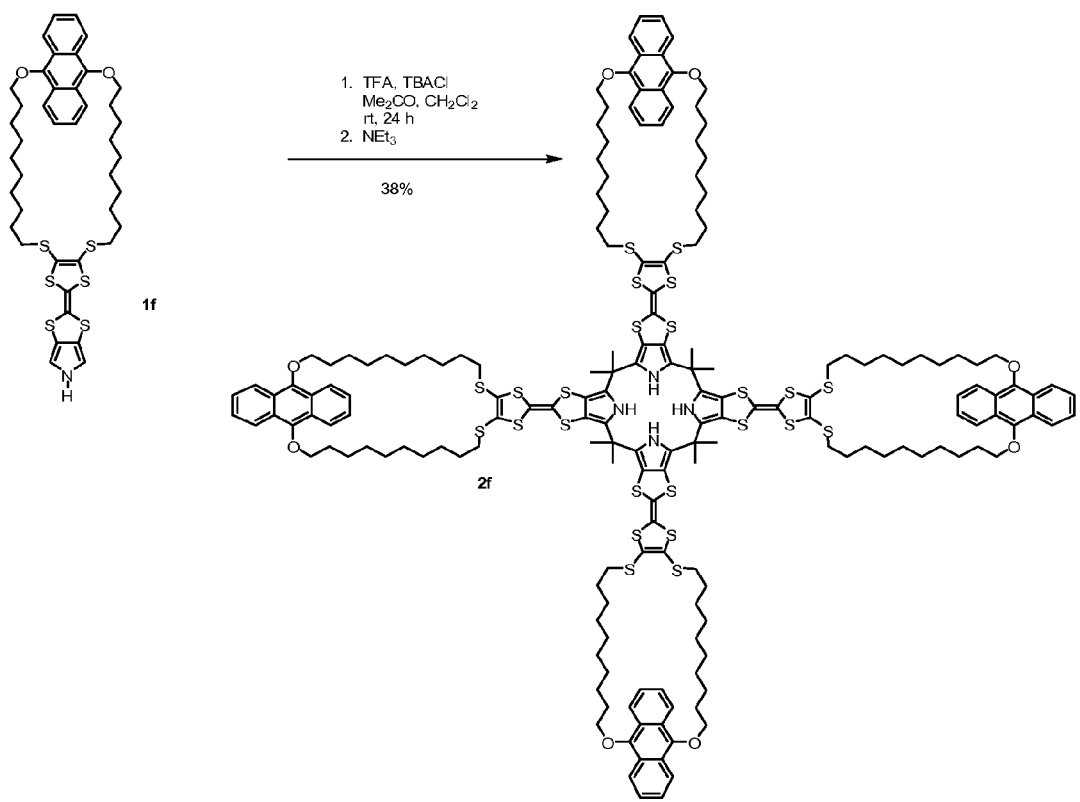
FIG. 15. Synthesis of the tetra-TTF calix[4]pyrrole derivative 2f.
Figure 16:
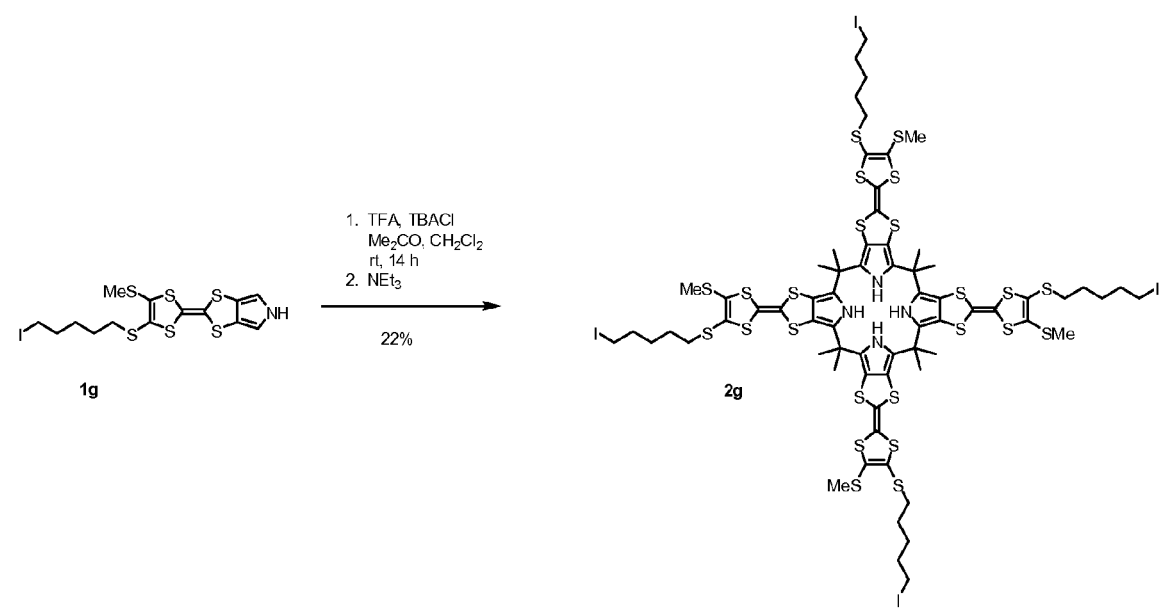
FIG. 16. Synthesis of the tetra-TTF calix[4]pyrrole derivative 2g.
Figure 17:
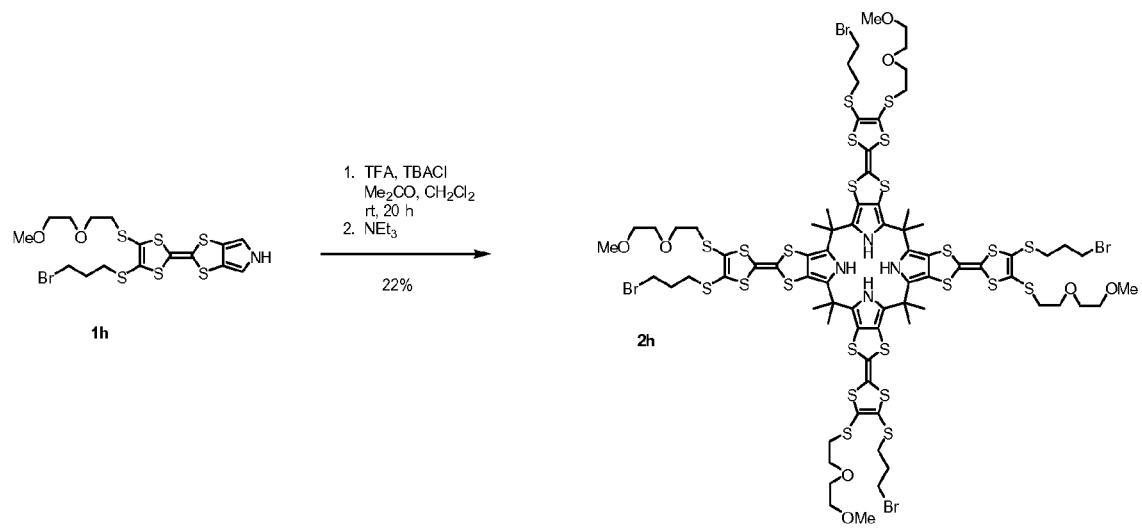
FIG. 17. Synthesis of the tetra-TTF calix[4]pyrrole derivative 2h.
Figure 18:
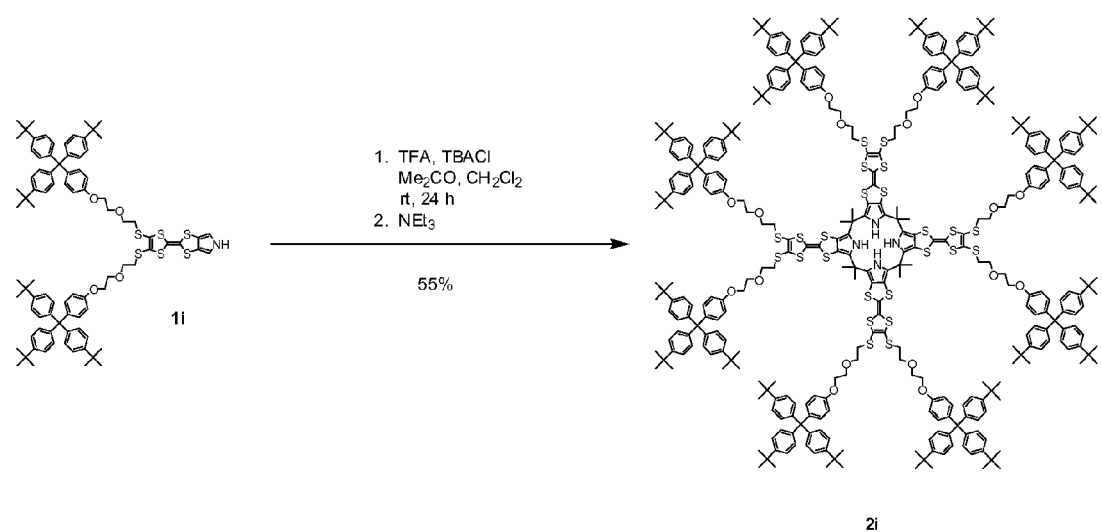
FIG. 18. Synthesis of the tetra-TTF calix[4]pyrrole derivative 2i.
Figure 19:
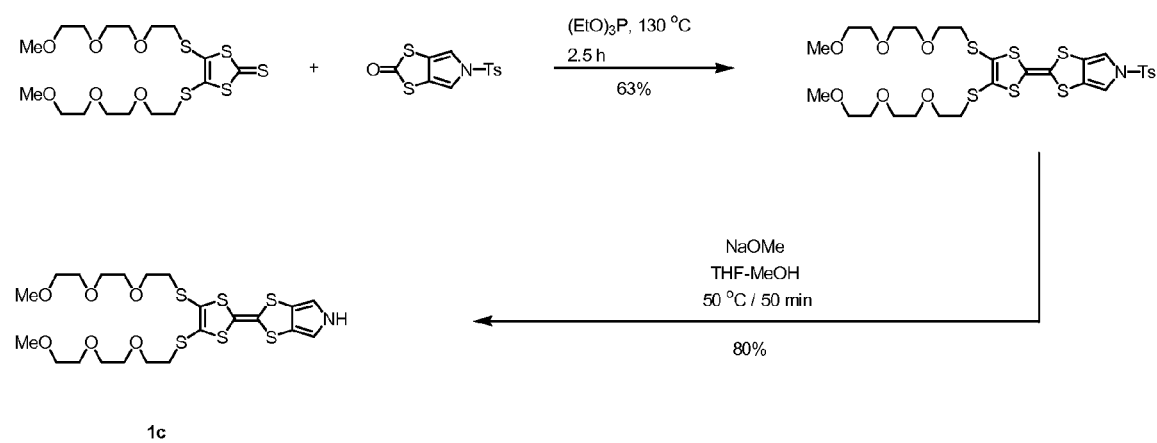
FIG. 19. Synthesis of the monopyrrolo-TTF derivative 1c.
Figure 20:
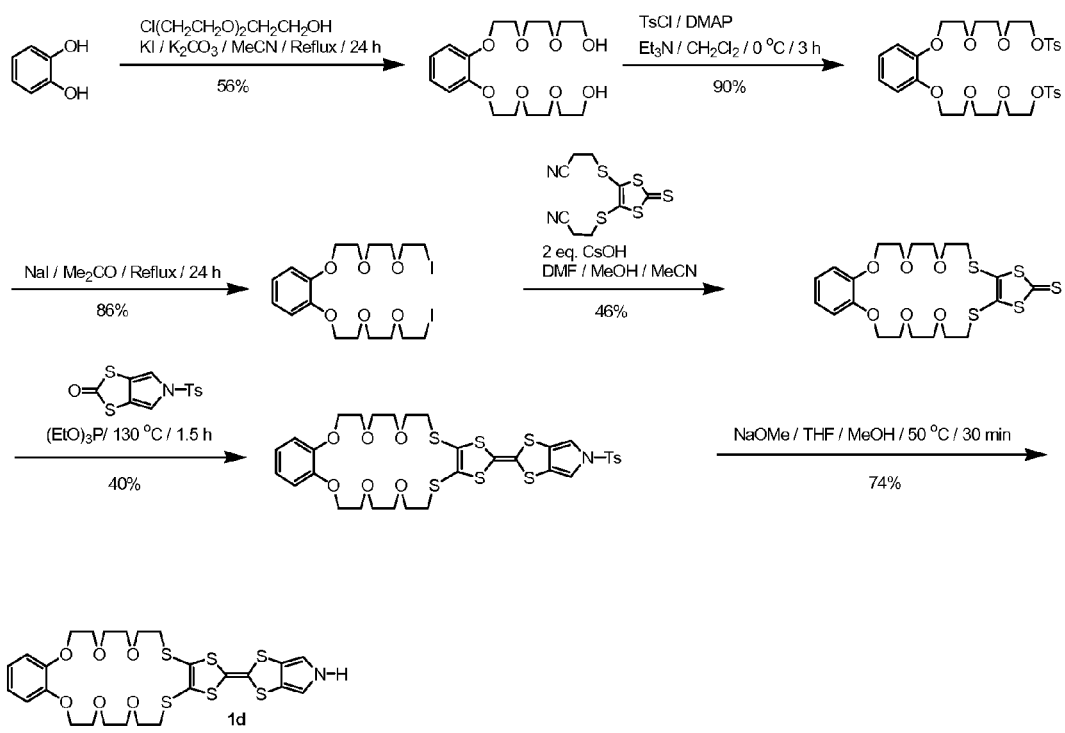
FIG. 20. Synthesis of the monopyrrolo-TTF derivative 1d.
Figure 21:
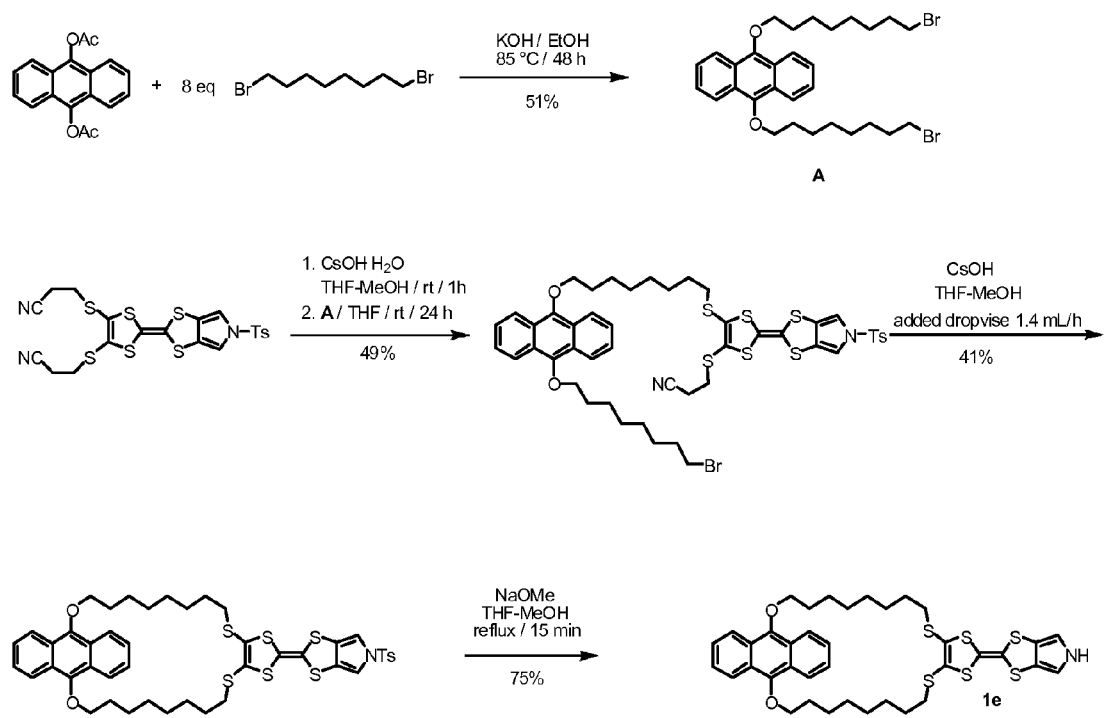
FIG. 21. Synthesis of the monopyrrolo-TTF derivative 1e.
Figure 22:
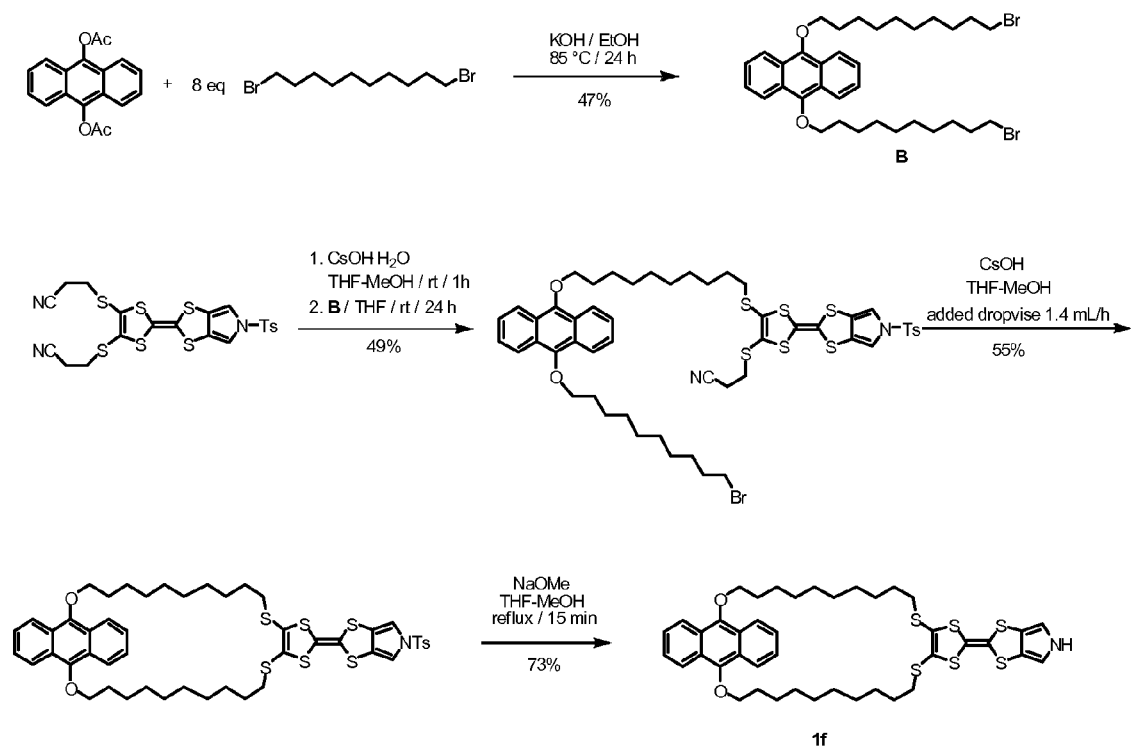
FIG. 22. Synthesis of the monopyrrolo-TTF derivative 1f.
Figure 23:
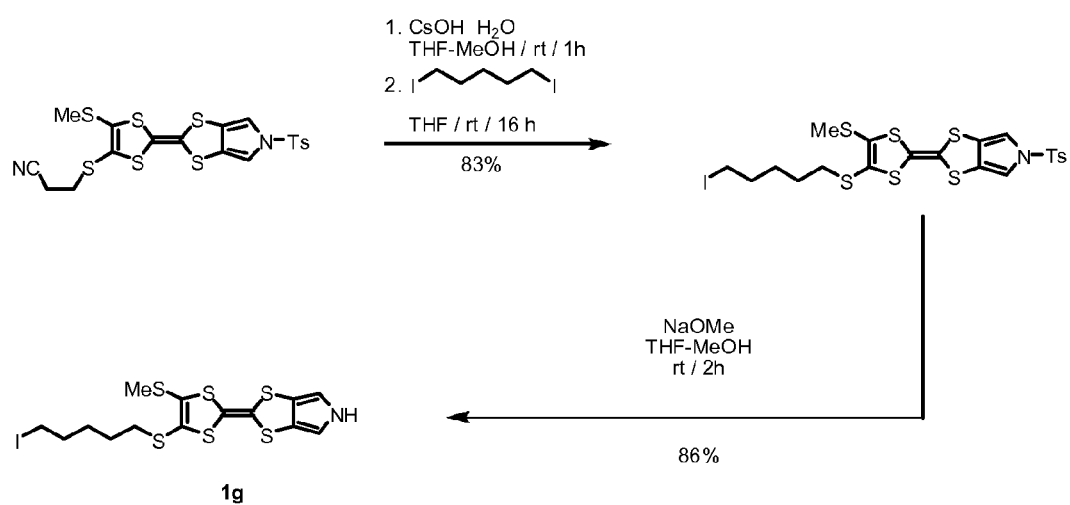
FIG. 23. Synthesis of the monopyrrolo-TTF derivative 1g.
Figure 24:
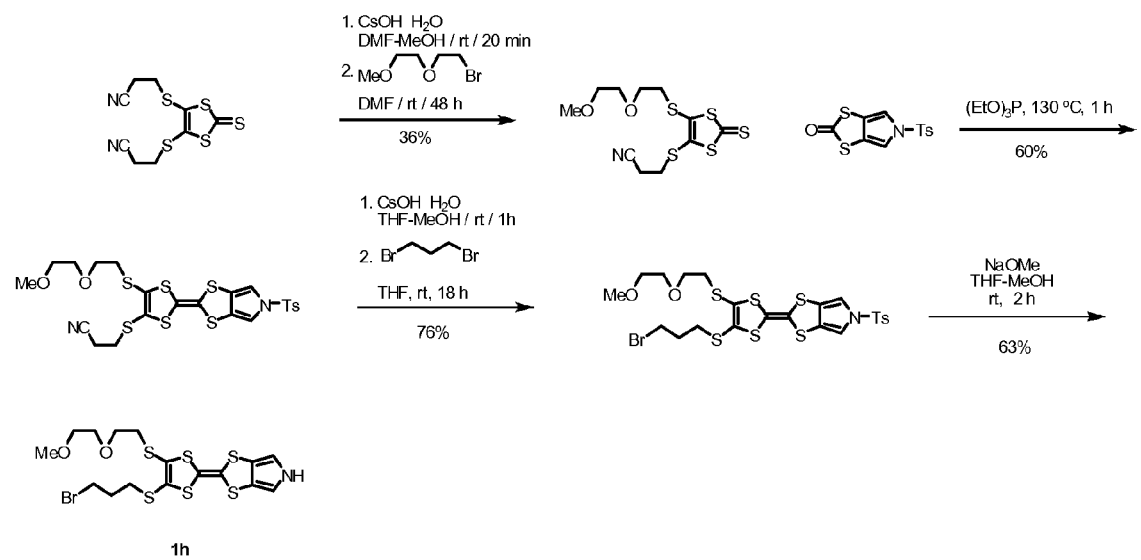
FIG. 24. Synthesis of the monopyrrolo-TTF derivative 1h.
Figure 25:
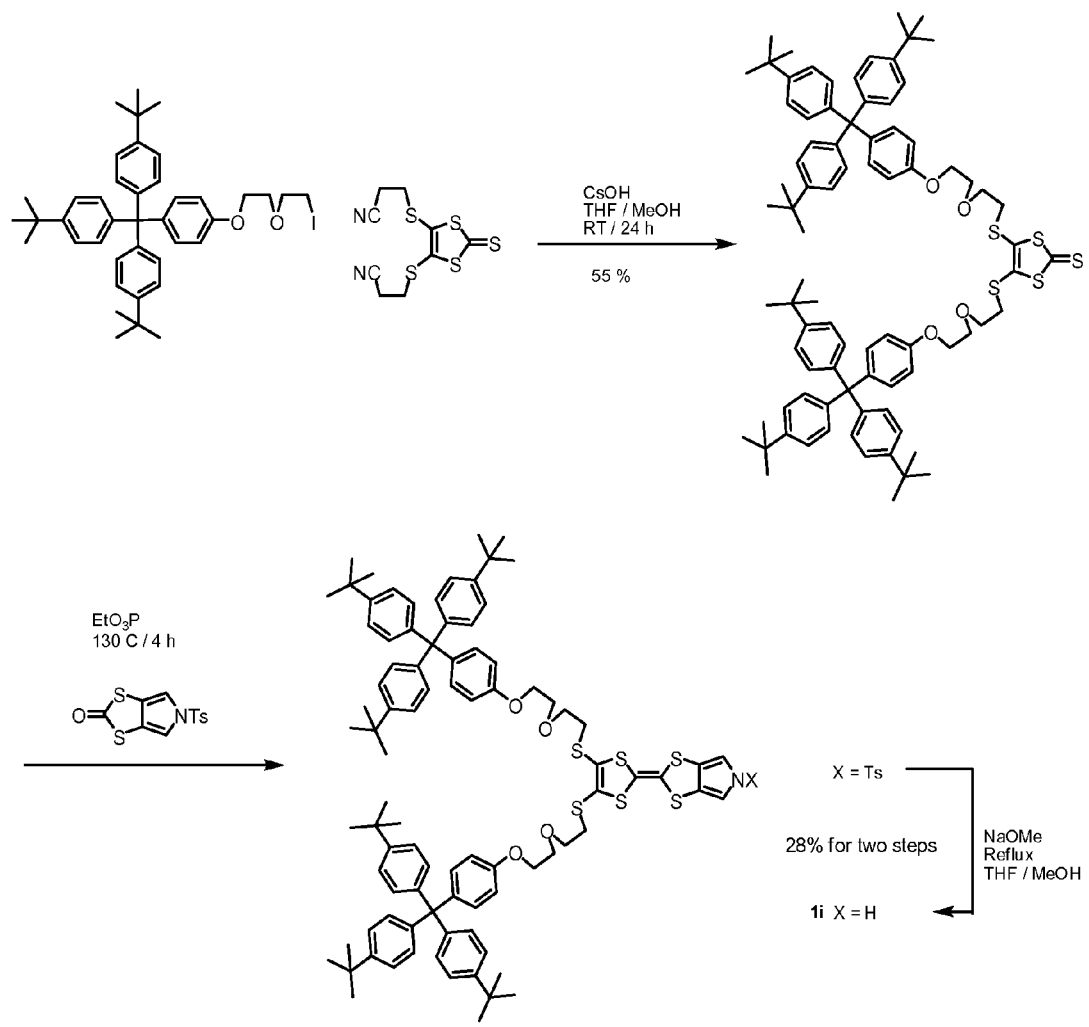
FIG. 25. Synthesis of the monopyrrolo-TTF derivative 1i.

Initial evidence for the interaction between tetra-TTF calix[4]pyrrole 2a and TNB and between tetra-TTF calix[4]pyrrole 2a and TNT came from X-ray crystallography. Diffraction-grade crystals were grown by slow diffusion of a pentane layer into a $CH_2Cl_2$ solution containing tetra-TTF calix[4]pyrrole 2a and TNB or TNT in a 1:2 ratio. The resulting structural analysis (FIG. 2) for the complexation between 2a an TNB revealed a solid-state structure containing two different tetra-TTF calix[4]pyrrole 2a units. Each of these complexes contains two guest molecules TNB, having two of their nitro groups pointing toward the NH protons, and are involved in hydrogenbonding interactions in the solid state. In the second complex, one guest molecule has two of its nitro groups oriented toward the NH protons, whereas the second guest has only one nitro group oriented toward the NH protons. In both of these complexes, the interplanar distance between pairs of TTFs is in the range of 6.80-7.10 Å. The resulting structural analysis (FIG. 3) for the complexation between 2a an TNT revealed a solid-state structure containing one tetra-TTF calix[4]pyrrole 2a unit and two guest molecules TNT, have two of their nitro groups pointing toward the NH protons, and are involved in hydrogenbonding interactions in the solid state. In this complex, the interplanar distance between pairs of TTFs is in the range of 6.90-7.50 Å. Addition of 2 equiv of TNB or TNT to a $CH_2Cl_2$ solution of tetra-TTF calix[4]pyrrole 2a resulted in an immediate color change from yellow to green and the appearance of a absorption bands centered at $\lambda=677$ nm (TNB) and $\lambda=625$ nm (TNT) in the UV-vis spectrum. This observation is thought to reflect the presence of CT interactions between the donor and the acceptor units present in tetra-TTF calix[4]pyrrole 2a and TNB or TNT, respectively. Addition of an anion to the tetra-TTF calix[4]pyrrole shifted the equilibrium from the 1,3-alternate to the corresponding cone conformation. Addition of 5 equiv of TBACl to a $CH_2Cl_2$ solution containing tetra-TTF calix[4]pyrrole 2a and TNB or TNT gave rise to a color change from green back to yellow and the disappearance of the absorption band centered at $=677$ nm (TNB) and $\lambda=625$ nm (TNT) in the UV-vis spectra (FIGS. 5 and 6). Addition of chloride ions to the solution of the tetra-TTF calix[4]pyrrole 2a and TNB or TNT resulted in a competition between the chloride ions and the electron-deficient guests for hydrogenbonding interactions with the NH protons of tetra-TTF calix[4]pyrrole 2a and therefore a competition between the 1,3-alternate conformation and the cone conformation. However, because of the high binding constant between tetra-TTF calix[4]pyrrole 2a and chloride ions, the equilibrium was largely shifted in favor of the cone conformation. This, in turn, led to the release (Scheme 2) of the electron-deficient guests TNB or TNT since the cavities present in tetra-TTF calix[4]pyrrole 2a in its 1,3-alternate conformation were no longer available for binding. Extracting the TBACl salt from the organic $CH_2Cl_2$ phase by washing with $H_2O$ regenerated the tetra-TTF calix[4]pyrrole/TNB and tetra-TTF calix[4]pyrrole/TNT complexes, and as a consequence, the green color of the $CH_2Cl_2$ solution was reestablished. Presumably, the formation of the host-guest complex in the absence of anions is enhanced by hydrogen-bonding interactions between two NH protons from the host tetra-TTF calix[4]pyrrole 2a and one or two of the nitro groups present in guest TNB or TNT. Support for this hypothesis is evident from $^1H$ NMR spectroscopic analyses. For instance, the $^1H$ NMR spectrum ($CDCl_3$, 298 K) of tetra-TTF calix[4]pyrrole 2a reveals a signal resonating at $\delta=7.10$ ppm, which is assigned to the free NH protons. Upon addition of two equiv of TNB to this solution, the signals corresponding to the resonances of the NH protons are shifted to $\delta=7.79$ ppm as a result of hydrogen-bonding interactions to the guest(s). In this mixture, the CH protons of TNB are, presumably as a consequence of being sandwiched between two shielding TTF subunits, found to resonate at $\delta=9.20$ ppm. Upon addition of 5 equiv of TBACl, the CH resonance in TNB is observed essentially at its initial position $\delta=9.35$ ppm. Upon release of the guest(s) on the other hand, the NH protons of tetra-TTF calix[4]pyrrole are shifted further downfield (δ=10.80 ppm) as a result of hydrogen-bonding interactions occurring between the NH protons and the chloride ion.

Example 2

Synthesis of the Tetra-TTF Calix[4]Pyrroles 2a-i

The tetra-TTF calix[4]pyrroles 2a-i (porphyrinogen derivatives of the present invention) were synthesized as shown in Schemes 3-11, Treating the monopyrrolo-TTF derivatives 1a-i with an excess of TFA and in the presence or absence of tetrabutylamonium fluoride (TBAF), tetrabutylamonium chloride (TBACl), or tetrabutylamonium bromide (TBABr) in a mixture of $CH_2Cl_2$ and $Me_2CO$ gave the tetra-TTF calix[4]pyrroles 2a-i as yellow compounds in 13-55% yields. The tetra-TTF calix[4]pyrroles 2a-i were fully characterized by traditional techniques. The required monopyrrolo-TTF derivatives 1a-b were prepared according to the literature procedures (Hansen et al. *J. Mater. Chem.* 2004, 14, 179-184 and Jeppesen et al. *J. Org. Chem.* 2000, 65, 5794-5805), whereas the monopyrrolo-TTF derivatives 1c-i were prepared as illustrated in Schemes 12-18.

Example 3

Binding Studies Between the Tetra-TTF Calix[4]Pyrroles 2a-i and TNB

To gain further insight in the strength of the association between the tetra-TTF calix[4]pyrroles and TNB, the binding constants between TNB and some of the different tetra-TTF calix[4]pyrroles were determined using $^1$H NMR spectroscopic titration techniques. The findings from these studies are listed in Table 1 and indicate that tetra-TTF calix[4]pyrroles with aromatic substituents (as in 2e and 2i) have a higher affinity to TNB as compared to tetra-TTF calix[4]pyrroles without aromatic substituents (as in 2a).

TABLE 1

Binding constants between tetra-TTF calix[4]pyrroles 2a, 2c-f and TNB as determined by $^1$H NMR spectroscopy at 298 K.

| Tetra-TTF calix[4]pyrrole | $K_a^1$ $(M^{-1})^a$ | $K_a^2$ $(M^{-1})^a$ |
|---|---|---|
| 2a | 20 | 900 |
| 2c | 92 | 412 |
| 2d | 110 | 520 |
| 2e | 300 | 1000 |
| 2f | 200 | 1400 |

$^a$CDCl$_3$ solution of tetra-TTF calix[4]pyrroles 2a, 2c-f were titrated by adding a concentrated CDCl$_3$ solution of TNB which also contained the tetra-TTF calix[4]pyrroles in quest 2a or 2c-f at the initial concentration to account for dilution effects. The binding constants were elucidated using Conners equation for 1:2 complexation, the estimated errors were <15%.

Example 4

Binding Studies Between the Tetra-TTF Calix[4]Pyrrols 2a and Different Nitrated Aromatics Mixing the tetra-TTF calix[4]pyrroles 2a with the nitrated aromatic guests TNB, 1,3-DNB, TNT, 2,4-DNT, 2,6-DNT, TNP, and 2,4-DNP in either $CH_2Cl_2$ or $CHCl_3$ produced green colored solutions, whereas similar experiment carried out with the non-nitrated guest tetrafluoro p-benzoquinone produced a brown colored solution. The strength of the binding between TNB, 1,3-DNB, TNT, 2,4-DNT, 2,6-DNT, TNP, and 2,4-DNP were quantified using $^1$H NMR spectroscopic titration techniques and the results from these studies are summarized in Table 2.

TABLE 2

Binding constants between tetra-TTF calix[4]pyrrole 2a and the guests TNB, 1,3-DNB, TNT, 2,4-DNT, 2,6-DNT, TNP, and 2,4-DNP as determined by $^1$H NMR spectroscopy at 298 K.

| Guest | $K_a^1$ $(M^{-1})^a$ | $K_a^2$ $(M^{-1})^a$ |
|---|---|---|
| TNB | 20 | 900 |
| 1,3-DNB | 27 | 60 |
| TNT | 25 | 132 |
| 2,4-DNT | 25 | 49 |
| 2,6-DNT | 14 | 37 |
| TNP | 50 | 936 |
| 2,4-DNP | 39 | 76 |

$^a$CDCl$_3$ solutions of the tetra-TTF calix[4]pyrrole 2a were titrated by adding a concentrated CDCl$_3$ solution of guests in question (TNB, 1,3-DNB, TNT, 2,4-DNT, 2,6-DNT, TNP, and 2,4-DNP) which also contained tetra-TTF calix[4]pyrrole 2a at the initial concentration to account for dilution effects. The binding constants were elucidated using Conners equation for 1:2 complexation, the estimated errors were <15%.

Example 5

Detection of Explosives in Sand by the Naked Eye

Figure 7:
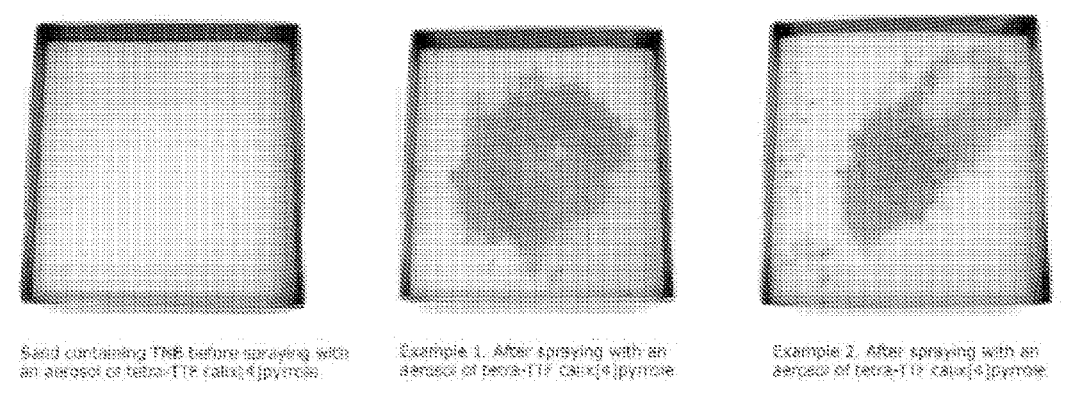

Sand containing a small quantity of TNB was deposited onto a closed area of sand without any TN B. Upon straying an aerosol of the tetra-TTF calix[4]pyrrole 2a dissolved in $CHCl_3$ unto the closed area of sand, a clear color change of the sand area containing TNB took place (FIG. 7).

The invention claimed is:
1. A compound of the formula 2

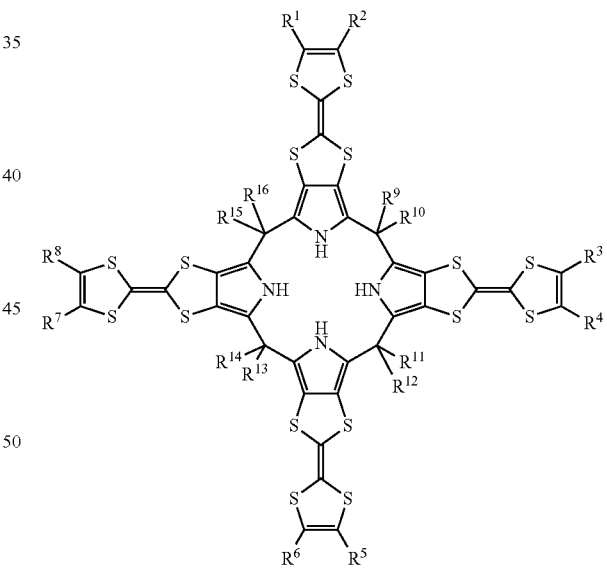

2 wherein $R^9$-$R^{16}$ each independently represents methyl, and wherein $R^1$-$R^8$ are each independently a member selected from the group consisting of
 i) $SR^A$ in which $R^A$ represents a —$CH_2CH_2O(CH_2CH_2O)_n$ group in which n=0-5;
 ii) $COOR^B$ in which $R^B$ represents an alkyl chain from C1 to C20 or a —$CH_2CH_2O(CH_2CH_2O)_n$ group in which n=0-5;
 iii) $CH_2Ar$, in which Ar represents an aryl group; and
 iv) $CH_2XR^C$ in which X represents and O, S, or N atom and $R^C$ represents an alkyl chain of from C1 to C20 or a —$CH_2CH_2O(CH_2CH_2O)_n$ group in which n=0-5.

2. A compound selected from the group consisting of:
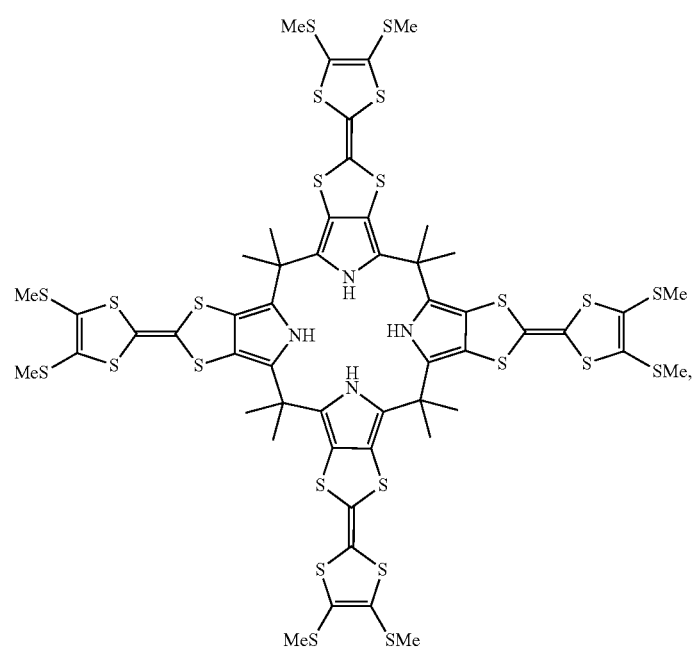
2b
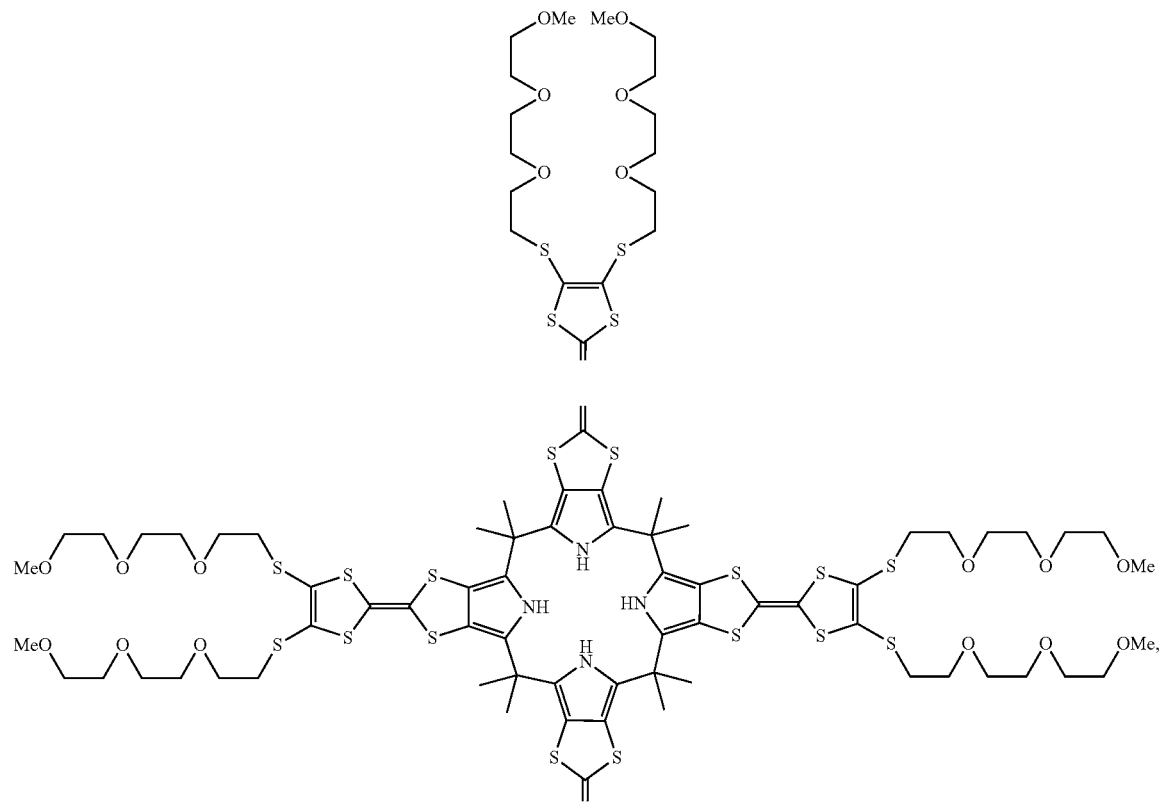
2c -continued
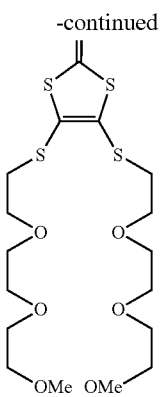
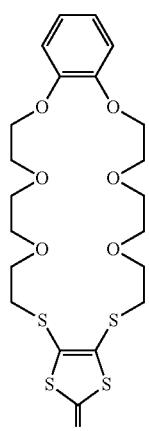
2d
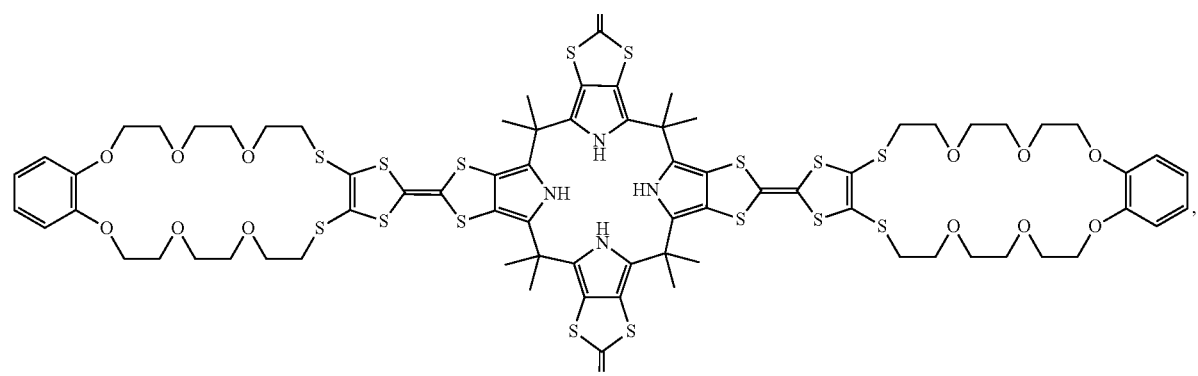
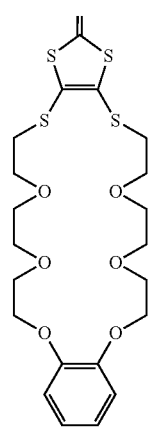

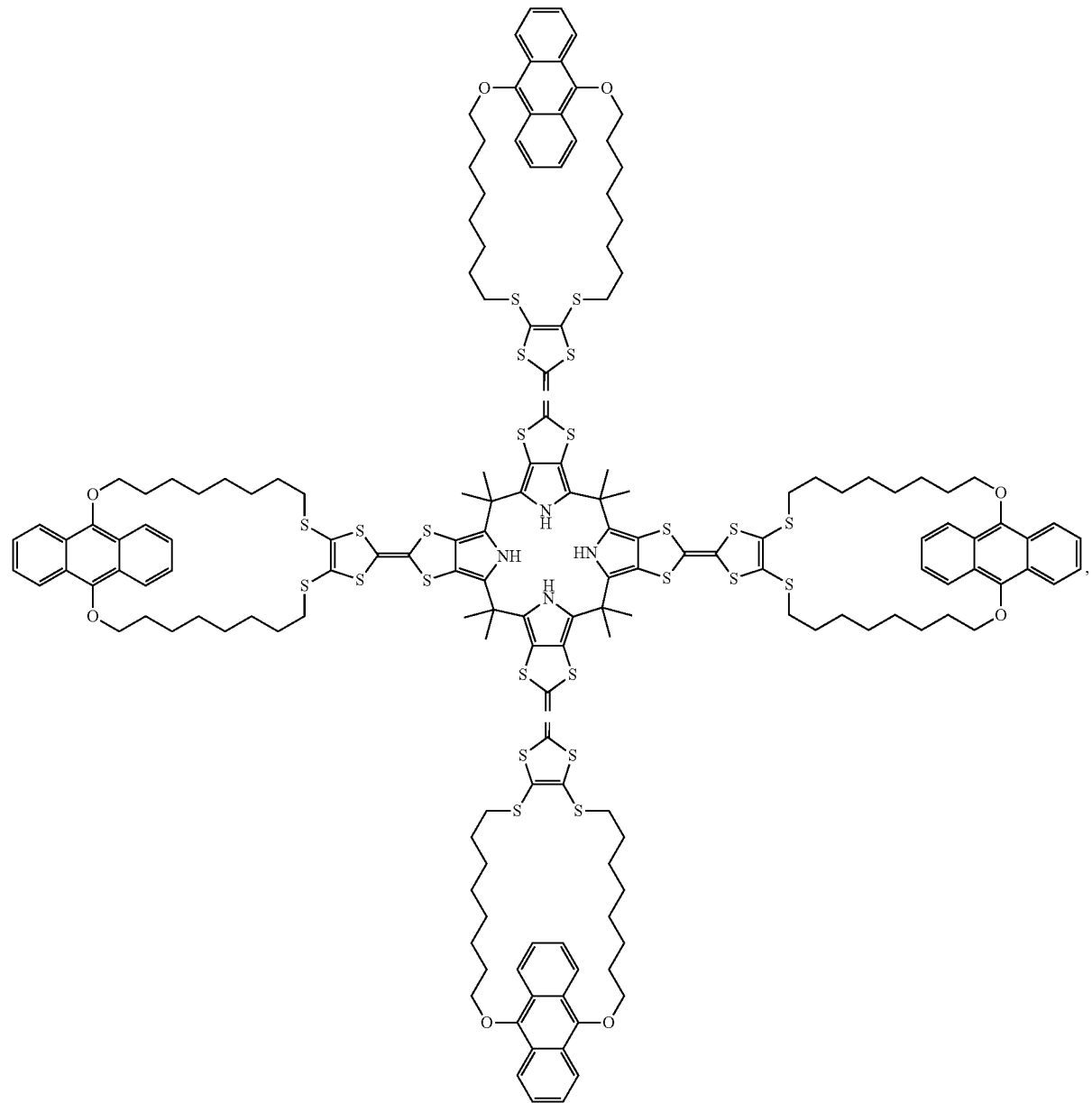
2e
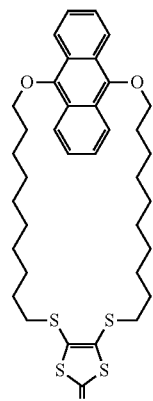
2f

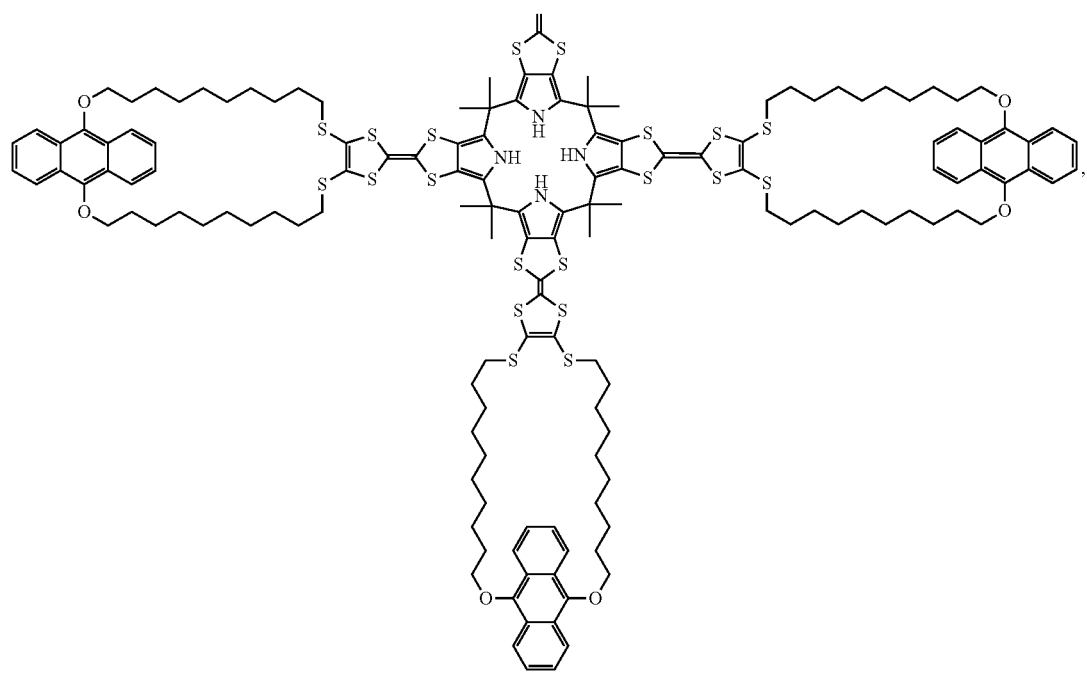
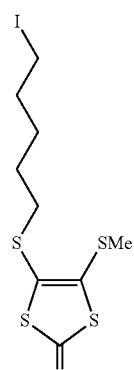
2g
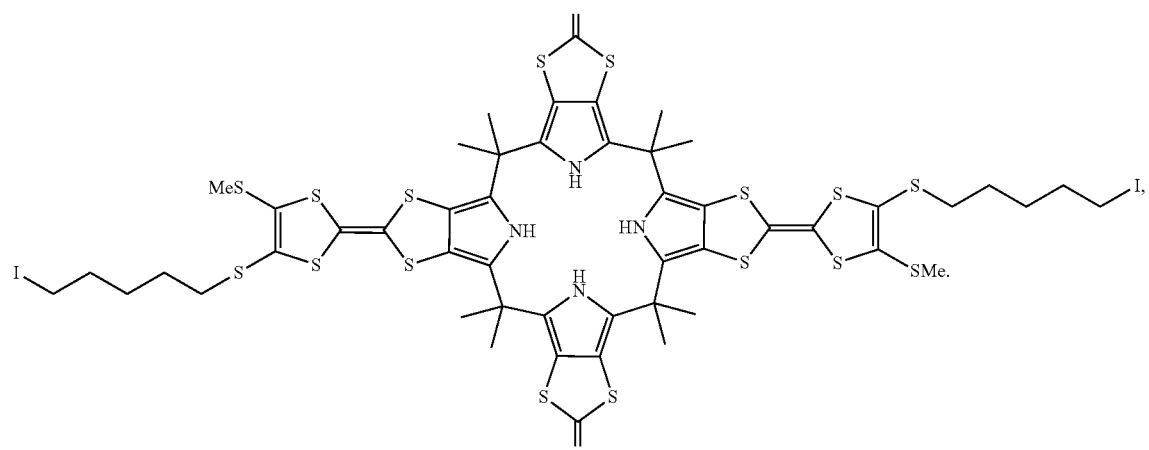

-continued
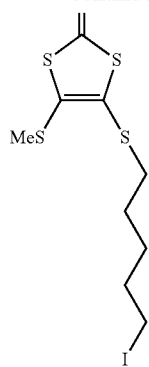
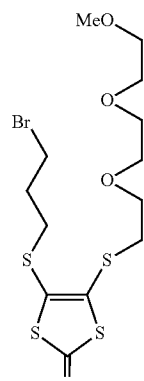
2h
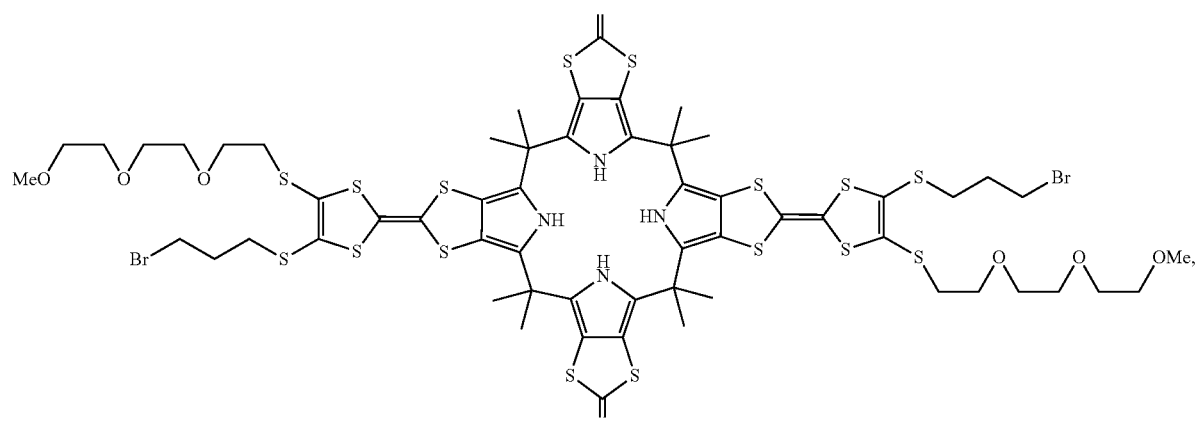
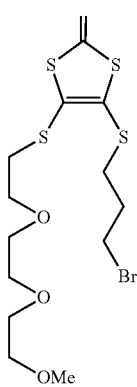

-continued
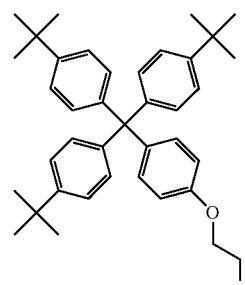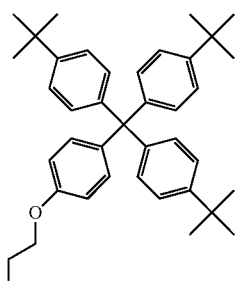
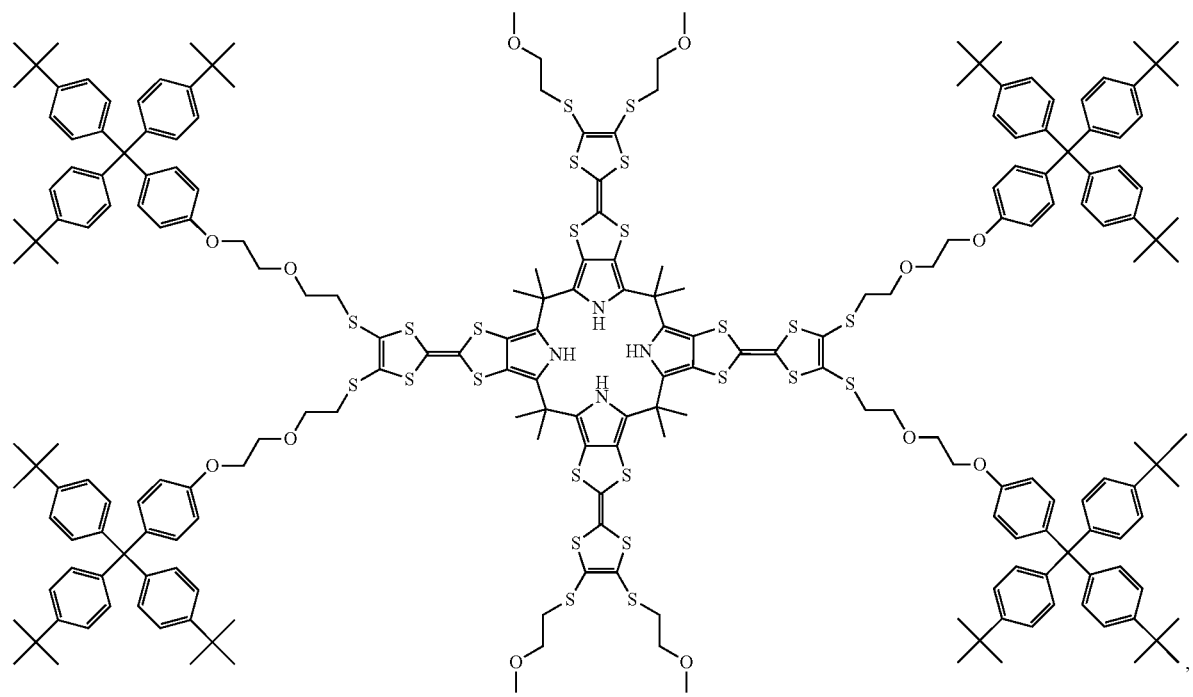
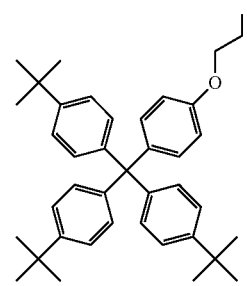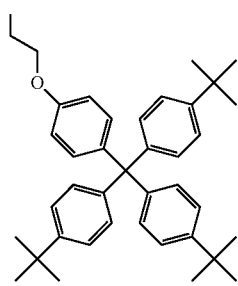
and

-continued

2j

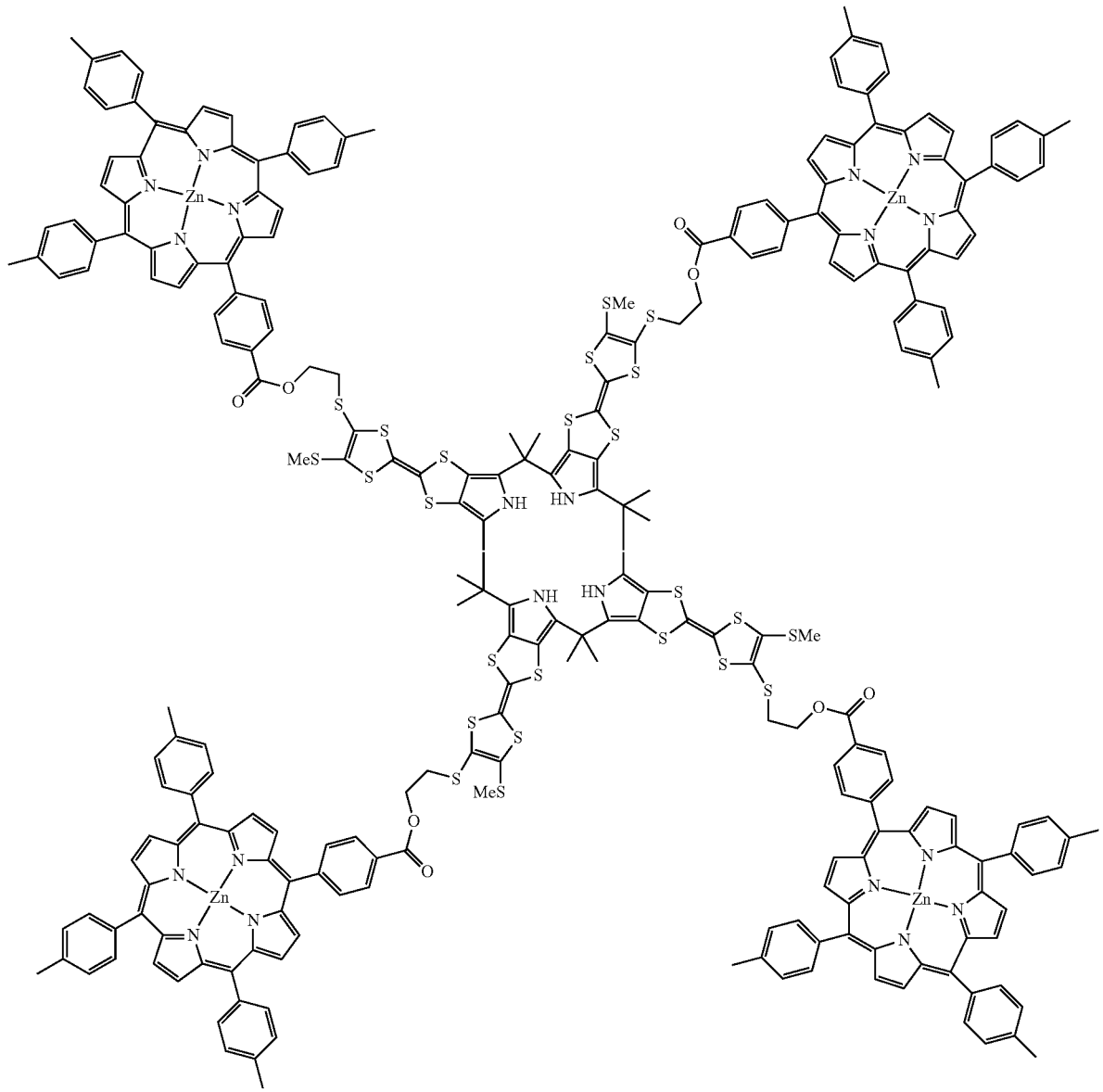

3. A kit for the detection of explosives comprising:
(i) at least one compound which undergoes a detectable change in absorption and/or emission of electromagnetic radiation when TNT, TNB, or TNP binds thereto; and
(ii) a detector capable of detecting any change in absorption and/or emission of electromagnetic radiation by the compound, said detected change being indicative of the presence of explosive in, on, or in association with said environment
wherein said compound is at least one porphyrinogen compound of claim 1 or 2.

4. A fiber optic sensor device for detecting the presence of a nitro-group containing explosive, the sensor comprising:
i) at least one optical fiber means having a proximal end and a distal end for transmitting light energy, the proximal end being disposed within a probe housing; a porphyrinogen compound of claim 1 or 2 disposed on the distal end of the optical fiber means, wherein the porphyrinogen derivative is capable of chemically binding with said nitro-group containing explosive;
ii) light source means for generating excitation energy, said light source means being operatively associated with said optical fiber means such that said excitation light passes through said optical fiber means; and
iii) detection means operatively associated with said optical fiber means, for detecting an emission signal generated by the porphyrinogen derivative.

5. The sensor device of claim 4, wherein the nitro-group containing explosive is selected from the group consisting of TNT, TNB, and TMP.

6. The sensor device of claim 5, wherein the light source means is selected from the group consisting of an argon laser, blue laser, tunable laser, and light emitting diode.

7. The sensor device of claim 6 wherein the detection means is selected from the group consisting of a spectrophotometer, spectrometer, photomultiplier tube, monochromator equipped with a CCD camera, filters, and the naked eye.

8. A method for detecting the presence of a target molecule comprising an explosive chemical comprising the steps of:
  i) exposing the porphyrinogen compound to an environment containing the explosive such that the explosive comes in contact with the porphyrinogen compound, and
  ii) detecting any change in absorption and/or emission of electromagnetic radiation by the porphyrinogen compound, said detected change being indicative of the presence of the explosive in, on or in association with said environment, wherein
  A) said compound is disposed on a distal end of at least one optical fiber capable of transmitting light energy;
  B) a light source for generating excitation energy is operatively associated with said optical fiber such that said excitation light passes through said optical fiber; and
  C) a detector is operatively associated with said optical fiber means, for detecting an emission signal generated by the compound,
  wherein said porphyrinogen compound is at least one porphyrinogen compound of claim 1 or 2.

9. The method of claim 8, wherein the explosive chemical is at least one member selected from the group consisting of TNT and TNB.

10. The method of claim 9, wherein the light source means is selected from the group consisting of an argon laser, blue laser, tunable laser, and light emitting diode.

11. The method of claim 10, wherein the detection means is selected from the group consisting of a spectrophotometer, spectrometer, photomultiplier tube, monochromator equipped with a CCD camera, quartz crystal microbalance (QCM), filters, and the naked eye.

12. A method for detecting an explosive, comprising:
  i) exposing at least one porphyrinogen compound of claim 1 or 2 to an environment containing explosive chemicals such that vapors and/or particulate emissions from the explosive come in contact with the porphyrinogen derivative; and
  ii) detecting any colour changes from yellow to green upon interaction with the explosive chemical.

13. A method for detecting an explosive, comprising
  i) exposing the porphyrinogen compound of the formula:

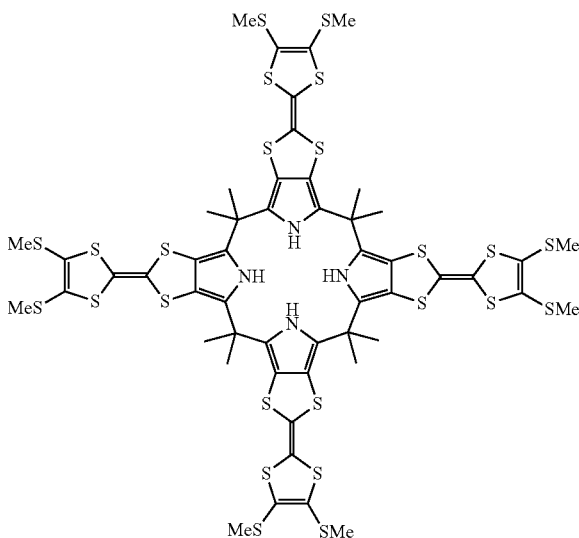

2b to an environment containing explosive chemicals such that vapors and/or particulate emissions from the explosive come in contact with the porphyrinogen compound; and
  ii) detecting any colour changes from yellow to green upon interaction with the explosive chemical.

* * * * *